United States Patent
Soto-Jara et al.

(10) Patent No.: US 6,462,171 B1
(45) Date of Patent: *Oct. 8, 2002

(54) PEPTIDES AND PHARMACEUTICAL COMPOSITIONS THEREOF FOR TREATMENT OF DISORDERS OR DISEASES ASSOCIATED WITH ABNORMAL PROTEIN FOLDING INTO AMYLOID OR AMYLOID-LIKE DEPOSITS

(75) Inventors: Claudio Soto-Jara, Geneva (CH); Marc H. Baumann, Helsinki (FI); Blas Frangione, New York, NY (US)

(73) Assignee: New York University, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/766,596

(22) Filed: Dec. 12, 1996

Related U.S. Application Data

(63) Continuation-in-part of application No. 08/630,645, filed on Apr. 10, 1996, now Pat. No. 5,948,763, which is a continuation-in-part of application No. 08/478,326, filed on Jun. 7, 1995, now abandoned.

(51) Int. Cl.⁷ .......................... A61K 38/00; C07K 16/00
(52) U.S. Cl. ...................... 530/326; 530/327; 530/238; 530/329; 530/330; 514/14; 514/15; 514/16; 514/17; 514/18
(58) Field of Search ............... 514/2, 12, 13, 514/14, 15, 16, 17, 18; 530/300, 324, 325, 326, 327, 328, 330, 331, 350

(56) References Cited

U.S. PATENT DOCUMENTS

| | | | |
|---|---|---|---|
| 5,169,933 A | * | 12/1992 | Anderson et al. |
| 5,817,626 A | | 10/1998 | Findeis et al. |
| 5,854,204 A | | 12/1998 | Findeis et al. |
| 5,854,215 A | | 12/1998 | Findeis et al. |
| 5,935,778 A | * | 8/1999 | Seidel et al. |
| 5,985,242 A | | 11/1999 | Findeis et al. |

FOREIGN PATENT DOCUMENTS

| | | | |
|---|---|---|---|
| EP | 359347 | * | 8/1990 |
| EP | 0584452 | * | 2/1994 |
| JP | 8119996 | * | 11/1996 |
| WO | 9404171 | * | 3/1994 |
| WO | WO 96/28471 | | 9/1996 |
| WO | WO 97/21728 | | 6/1997 |

OTHER PUBLICATIONS

Borman, S., Science Jun. 17, 1996 pp. 33–34.*
Wille et al, Ciba Foundation Symposium, 199:181–201, 1996.*
Hilbich et al., J. Mol. Biol., 228:460–473, 1992.*
Pike et al, J. of Neurochemistry, 64(1):253–265, 1995.*
Tomiyama et al, BBRC, 204(1):76–83, 1994.*
Dobeli et al, Bio Technology, 13:988–993, Sep. 13, 1995.*
Wisniewski et al., BBRC, 179(3):1247–1245, 1991.*
Rudinger, J. in "Peptide Hormones", University Park Press, Baltimore, Jun. 1976, pp. 1–7.*
Soto et al, "Two Conformational States of Amyloid beta–Peptide: Implications for the Pathogenesis of Alzheimer's Disease," *Neuroscience Letters*, 186:115–118 (1995).
Soto et al, "The alpha–Helical to beta–Strand Transition in the Amino–Terminal Fragment of the Amyloid beta–Peptide Modulates Amyloid Formation", *J. of Biochem.*, 20(7):3063–3067 (1995).
Soto et al, "Structural Determinants of the Alzheimer's beta–Peptide", *J. of Neurochem.*, 63:1191–1198 (1994).
Wood et al, "Prolines and Amyloidgenicity in Fragments of the Alzheimers Peptide beta/A4", *Biochemistry*, 34:724–730 (1995).

* cited by examiner

*Primary Examiner*—Patricia A. Duffy
(74) *Attorney, Agent, or Firm*—Browdy and Neimark

(57) ABSTRACT

Novel peptides capable of interacting with a hydrophobic β-sheet forming cluster of amino acid residues on a protein or peptide for amyloid or amyloid-like deposit formation inhibit and structurally block the abnormal folding of proteins and peptides into amyloid or amyloid-like deposits and into pathological β-sheet-rich conformation as precursors thereof. Methods for preventing, treating or detecting disorders or diseases associated with amyloid-like fibril deposits, such as Alzheimer's disease and prion-related encephalopathies, are also provided.

16 Claims, 22 Drawing Sheets

| PROTEIN | AMINO ACID SEQUENCE |
|---|---|
| ALZHEIMER'S β-AMYLOID | 16 K L V F F A̲ E̲ D 23 |
| AMYLOID A | 1 R S F F S F L G 8 |
| GELSOLIN AMYLOID | 187 D̲ C F I L D L G 194 |
| AMYLOID L | 18 R V T I T C Q A 25 |
| β2-MICROGLOBULIN AMYLOID | 61 S F Y L L Y Y T 68 |
| APOLIPOPROTEIN A1 AMYLOID | 13 D L A T V Y V D 20 |

ANTI-AMYLOID 1　　　　SRGDLPFFPVPIGDS
ANTI-AMYLOID 2　　　　RDLPFFPVPID
ANTI-AMYLOID 3　　　　RDFIPLPLD
ANTI-AMYLOID 4　　　　RDYLPYYPLD

FIG. 6A
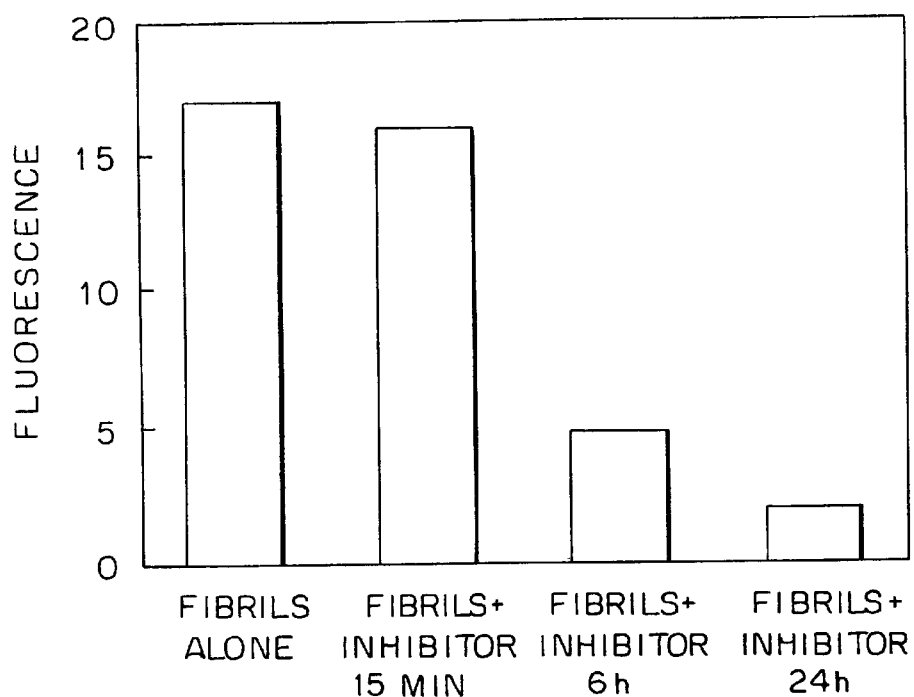
FIG. 7A
| PROTEIN | AMINO ACID SEQUENCE |
|---|---|
| AMPHOTERIN (HMG-1) | 10 G K M S S Y A F F V Q T C R E E H K 27 |
FIG. 7B
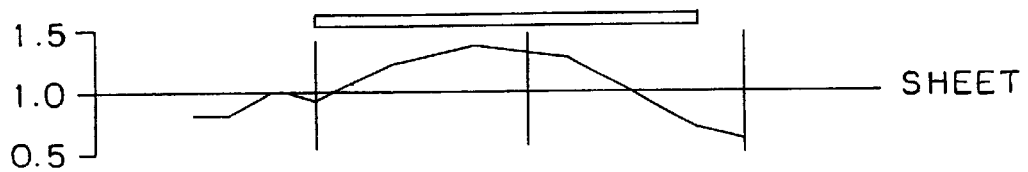
SHEET

PrP109-141 incubated alone

PrP109-141 incubated with iPrP-12aa

PEPTIDES AND PHARMACEUTICAL COMPOSITIONS THEREOF FOR TREATMENT OF DISORDERS OR DISEASES ASSOCIATED WITH ABNORMAL PROTEIN FOLDING INTO AMYLOID OR AMYLOID-LIKE DEPOSITS

CROSS-REFERENCE TO RELATED APPLICATION

The present application is a continuation-in-part of U.S. application Ser. No. 08/630,645, filed Apr. 10, 1996, now U.S. Pat. No. 5,948,763, which application is a continuation-in-part of U.S. application Ser. No. 08/478,326, filed Jun. 7, 1995, now abandoned, the entire contents of both of which are hereby incorporated by reference.

GOVERNMENT LICENSE RIGHTS

The U.S. Government has a paid-up license in this invention and the right in limited circumstances to require the patent owner to license others on reasonable terms as provided for by the terms of Grant No. 10953 awarded by National Institutes of Health.

BACKGROUND OF THE INVENTION

1. Field of the Invention

This invention relates to the field of therapeutic peptides for the prevention and treatment of disorders or diseases resulting from abnormal formation of amyloid or amyloid-like deposits, such as, but not limited to, prion-related encephalopathies, Alzheimer's dementia or disease (AD), and other amyloidosis disorders. This invention also relates to the use of the peptides in preventing the formation of or in promoting the redissolution of these insoluble amyloid or amyloid-like deposits.

2. Description of the Background Art

Alzheimer's disease (AD) is the most common form of dementia in adults (C. Soto et al. *J. Neurochem.* 63:1191–1198, 1994), constituting the fourth leading cause of death in the United States. Approximately 10% of the population over 65 years old is affected by this progressive degenerative disorder that is characterized by memory loss, confusion and a variety of cognitive disabilities. One of the key events in AD is the deposition of amyloid as insoluble fibrous masses (amyloidogenesis) resulting in extracellular neuritic plaques and deposits around the walls of cerebral blood vessels. The main component of amyloid is a 4.1–4.3 kDa hydrophobic peptide, named amyloid β-peptide (Aβ), that is codified in chromosome 21 as part of a much longer amyloid precursor protein APP (Muller-Hill and Beyreuther, *Ann. Rev. Biochem.* 38:287–307, 1989). The APP starts with a leader sequence (signal peptide), followed by a cysteine-rich region, an acidic-rich domain, a protease inhibitor motif, a putative N-glycosylated region, a transmembrane domain, and finally a small cytoplasmic region. The Aβ sequence begins close to the membrane on the extracellular side and ends within the membrane. Two-thirds of Aβ faces the extracellular space, and the other third is embedded in the membrane (Kang et al. *Nature* 325:503–507, 1987; Dyrks et al. *EMBO J.* 7:949–957, 1988). Several lines of evidence suggest that amyloid may play a central role in the early pathogenesis of AD.

Evidence that amyloid may play an important role in the early pathogenesis of AD comes primarily from studies of individuals affected by the familial form of AD (FAD) or by Down's syndrome. Down's syndrome patients have three copies of APP gene and develop AD neuropathology at an early age (Wisniewski et al., *Ann. Neurol.* 17:278–282, 1985). Genetic analysis of families with hereditary AD revealed mutations in chromosome 21, near or within the Aβ sequence (Forsell et al., *Neurosci. Lett.* 184:90–93, 1995). Moreover, recently it was reported that transgenic mice expressing high levels of human mutant APP progressively develop amyloidosis in brain (Games et al., *Nature* 373:523–527, 1995). These findings appear to implicate amyloidogenesis in the pathophysiology of AD.

Recently, the same peptide that forms amyloid deposits in AD brain was also found in a soluble form (sAβ) normally circulating in the human body fluids (Seubert et al., Nature 359:355–327, 1992; Shoji et al., *Science* 258:126–129, 1992). Zlokovic et al., *Biochem. Biophys. Res. Commun.* 205:1431–1437 (1994), reported that the blood-brain barrier (BBB) has the capability to control cerebrovascular sequestration and transport of circulating sAβ, and that the transport of the sAβ across the BBB was significantly increased when sAβ was perfused in guinea pigs as a complex with apolipoprotein J (apoJ). The sAβ-apoJ was found in normal cerebrospinal fluid (CSF; Ghiso et al. Biochem. J. 293:27–30, 1994) and in vivo studies indicated that sAβ is transported with apoJ as a component of the high density lipoproteins (HDL) in normal human plasma (Koudinov et al., *Biochem. Biophys. Res. Commun.* 205:1164–1171, 1994). It was also recently reported by Zlokovic et al., *Proc. Natl. Acad. Sci. USA* 93:4229–04233 (1996), that the transport of sAβ across the BBB was almost abolished when the apoJ receptor gp330 was blocked. It is believed that the conversion of sAβ to insoluble fibrils is initiated by a conformational or proteolytic modification of the 2–3 amino acid longer soluble form. It has been suggested that the amyloid formation is a nucleation-dependent phenomena in which the initial insoluble "seed" allows the selective deposition of amyloid (Jarrett et al., *Biochem.* 32 :4693–4697, 1993).

Peptides containing the sequence 1-40 or 1-42 of Aβ and shorter derivatives can form amyloid-like fibrils in the absence of other protein (Soto et al., *J. Neurochem.* 63:1191–1198, 1994), suggesting that the potential to form amyloid resides mainly in the structure of Aβ. The relation between the primary structure of Aβ and its ability to form amyloid-like fibrils was analyzed by altering the sequence of the peptide. Substitution of hydrophilic residues for hydrophobic ones in the internal Aβ hydrophobic regions (amino acids 17–21) impaired fibril formation (Hilbich et al.,*J. Mol. Biol.* 228:460–473, 1992), suggesting that Aβ assembly is partially driven by hydrophobic interactions. Indeed, larger Aβ peptides (Aβ1-42/43) comprising two or three additional hydrophobic C-terminal residues are more amyloidogenic (Jarrett et al., *Biochem* 32:4693–4697, 1993). Secondly, the conformation adopted by Aβ peptides is crucial in amyloid formation. Aβ incubated at different pH, concentrations and solvents has mainly an a-helical (random coil) or a β-sheet secondary structure (Barrow et al., *J. Mol. Biol.* 225:1075–1093, 1992: Burdick'et al., *J. Biol. Chem.* 267:546–554, 1992; Zagorski et al., *Biochem.* 31:5621–5631, 1992). The Aβ peptide with α-helical or random coil structure aggregates slowly; Aβ with β-sheet conformation aggregates rapidly (Zagorski et al.,*Biochem*. 31:5621–5631, 1992; Soto et al., *J. Biol. Chem.* 270:3063–3067, 1995; Soto and Castano, *Biochem. J.* 314:701–707, 1996). The importance of hydrophobicity and β-sheet secondary structure on amyloid formation also is suggested by comparison of the sequence of other amyloidogenic proteins.

Analysis of Aβ aggregation by turbidity measurements indicates that the length of the C-terminal domain of Aβ influences the rate of Aβ assembly by accelerating nucleus formation (Jarrett et al., *Cell* 73:1055–1058, 1993 ). Thus, the C-terminal domain of Aβ may regulate fibrillogenesis. However, in vitro modulators of Aβ amyloid formation, such as metal cations (Zn, Al) (Bush et al., *Science* 265:1464–1467, 1994; Exley et al., *FEBS Lett.* 324:293–295, 1993) heparin sulfate proteoglycans, and apoliprotein E (Strittmatter et al., *Proc. Natl. Acad. Sci. USA* 90:1977–1981, 1993) interact with the 12–28 region of Aβ. Moreover, mutations in the β PP gene within the N-terminal Aβ domain yield analogs more fibrillogenic (Soto et al., 1995, supra; Wisniewski et al., *Biochem. Biophys. Res. Commun.* 179:1247–1254, 1991). Finally, while the C-terminal domain of Aβ invariably adopts a β-strand structure in aqueous solutions, environmental parameters determine the existence of alternative conformation in the Aβ N-terminal domain (Barrow et al., 1992, supra; Soto et al., 1995, supra; Burdick et al., 1992, supra). Therefore, the N-terminus may be a potential target site for inhibition of the initial random coil to β-sheet conformational change.

The emerging picture from studies with synthetic peptides is that Aβ amyloid formation is dependent on hydrophobic interactions of Aβ peptides adopting an antiparallel β-sheet conformation and that both the N- and C-terminal domains are important for amyloid formation. The basic unit of fibril formation appears to be the conformer adopting an antiparallel β-sheet composed of strands involving the regions 10-24 and 29-40/42 of the peptide (Soto et al., 1994, supra). Amyloid formation proceeds by intermolecular interactions between the β-strands of several monomers to form an oligomeric β-sheet structure precursor of the fibrillar β-cross conformation. Wood et al., *Biochemistry* 34:724–730 (1995), reported the insertion of aggregation-blocking prolines into amyliod proteins and peptides, as exemplified by test peptides having the amino acid sequences of SEQ ID NOs:50–65, to prevent aggregation of such proteins and peptides. In this manner, the authors suggest that novel proteins can be designed to avoid the problem of aggregation as a barrier to their production without affecting the structure or function of the native protein. Thus, Wood et al. seek to produce novel proteins that would not aggregate during recombinant protein production and purification by inserting aggregation-blocking prolines into these novel prolines. The inhibitory peptides of the present invention, which inhibit the formation of amyloid deposits from native Aβ as opposed to solely preventing aggregation of a proline-modified peptide or protein, are not intended to include the peptides of Wood et al. having the amino acid sequences SEQ ID NOs:50–65.

To date there is no cure or treatment for AD and even the unequivocal diagnosis of AD can only be made after post-mortem examination of brain tissues for the hallmark neurofibrillary tangles (NFT) and neuritic plaques. However, there are several recent publications outlining strategies for the treatment of Alzheimer's disease.

Heparin sulfate (glycosoaminoglycan) or the heparin sulfate proteoglycan, perlecan, has been identified as a component of all amyloids and has also been implicated in the earliest stages of inflammation-associated amyloid induction. Kisilevsky et al., *Nature Medicine* 1(2):143–148, (1995) describes the use of low molecular weight (135–1, 000 Da) anionic sulfonate or sulfate compounds that interfere with the interaction of heparin sulfate with the inflammation-associated amyloid precursor and the β-peptide of AD. Heparin sulfate specifically influences the soluble amyloid precursor (SAA2) to adopt an increased β-sheet structure characteristic of the protein-folding pattern of amyloids. These anionic sulfonate or sulfate compounds were shown to inhibit heparin-accelerated Alzheimer's Aβ fibril formation and were able to disassemble preformed fibrils in vitro as monitored by electron micrography. Moreover, when administered orally at relatively high concentrations (20 or 50 mM), these compounds substantially arrested murine splenic inflammation-associated amyloid progression in vivo in acute and chronic models. However, the most potent compound, poly- (vinylsulfonate), was acutely toxic.

Anthracycline 4'-iodo-4'-deoxy-doxorubicin (IDOX) has been observed clinically to induce amyloid resorption in patients with immunoglobin light chain amyloidosis (AL) Merlini et al., Proc. Natl. Acad. Sci. USA 92:2959–2963 (1995), elucidated its mechanism of action. IDOX was found to bind strongly via hydrophobic interactions to two distinct binding sites (Scatchard analysis) in five different tested amyloid fibrils, inhibiting fibrillogenesis and the subsequent formation of amyloid deposits in vitro. Preincubation of IDOX with amyloid enhancing factor (AEF) also reduced the formation of amyloid deposits. Specific targeting of IDOX to amyloid deposits in vivo was confirmed in an acute murine model. This binding is distinct from heparin sulfate binding as removal of the glycosaminoglycans from extracted amyloid fibrils with heparinases did not modify IDOX binding. The common structural feature of all amyloids is a β-pleated sheet conformation. However, IDOX does not bind native amyloid precursor light chains which suggests that the β-pleated sheet backbone alone is not sufficient to form the optimal structure for IDOX binding, and that it is the fibril cross-β-sheet quaternary structure that is required for maximal IDOX binding. It has been found that the amount of IDOX extracted from spleens is correlated with amyloid load and not circulating serum precursor amyloid levels. IDOX, however, is also extremely toxic.

The regulation and processing of amyloid precursor protein (APP) via inhibition or modulation of phosphorylation of APP control proteins has also been investigated in U.S. Pat. No. 5,385,915 and WO 9427603. Modulating proteolytic processing of APP to nucleating forms of AD has also been examined in AU 9338358 and EP569777. WO 95046477 discloses synthetic peptides of composition X-X-N-X (SEQ ID NO:69) coupled to a carrier, where X is a cationic amino acid and N is a neutral amino acid, which inhibit Aβ binding to glycosoaminoglycan. Peptides containing Alzheimer's Aβ sequences that inhibit the coupling of α-1-antichymotrypsin and Aβ are disclosed in WO 9203474.

Prions are the infectious particles responsible for a group of fatal neurodegenerative diseases known as spongiform encephalopathies (for reviews, see Prusiner & DeArmond, *Annu. Rev. Neurosci.* 17:311–339, 1994; Prusiner, *Science* 252:1515–1522, 1991). Creutzfeldt-Jakob disease (CJD), kuru, Gerstmann-Straussler syndrome (GSS) and fatal familial insomnia are all human neurodegenerative diseases caused by prions and are frequently transmissible to laboratory animals. Familial CJD and GSS are also genetic disorders. In addition to the prion diseases in humans, four disorders of animals are included in this type of disease. Scrapie in sheep and goats is the most common of the prion diseases. Bovine spongiform encephalopathy (BSE), also known as the "mad cow disease", transmissible mink encephalopathy, and chronic wasting disease of captive mule deer and elk are all thought to result from the ingestion of scrapie-infected animal products.

To date there is no cure or effective treatment for prion-related diseases. The infectious agent causing prion-related diseases differ from bacteria, fungi, parasites, viroids and viruses in that no DNA is needed and it apparently only consists of protein. The principal component of prions is the glycoprotein called PrP$^{sc}$. Prion replication is hypothesized to occur when PrP$^{sc}$ in the infecting inoculum interacts specifically with host PrP$^c$ (normal cellular PrP isoform), catalyzing its conversion to the pathogenic form of the protein (Cohen, F. E. et al., *Science* 264:530–531, 1994). It is postulated that this conversion takes place spontaneously in PrP molecules carrying mutations that have been linked to familial forms of prion disease.

The cellular prion protein (PrP$^c$) is a sialoglycoprotein encoded by a gene that in humans is located on chromosome 20 (Oesch, B. et al., *Cell* 40:735–746, (1985); Basler, K. et al., 46:417–428 (1986); Liao, Y. J. et al., *Science* 233:364–367 (1986); Meyer, R. K. et al., *Proc. Natl. Acad. Sci. USA* 83:2310–2314 (1986); Sparkes, R. S. et al., *Proc. Natl. Acad. Sci. USA* 83:7358–7362 (1986); Bendheim, P. E. et al. *J. Infect. Dis.* 158:1198–1208 (1988); Turk, E. et al. *Eur. J. Biochem.* 176:21–30 (1988)). The PrP gene is expressed in neural and non-neural tissues, the highest concentration of mRNA being in neurons (Chesebro, B. et al., *Nature* 315:331–333 (1985); Kretzschmar, H. A. et al., *Am. J. Pathol.* 122:1–5 (1986); Brown, H. R. et al., *Acta Neuropathol.* 80:1–6 (1990); Cashman, N. R. et al., *Cell* 61:185–192 (1990); Bendheim, P. E., *Neurology* 42:149–156 (1992)).

The translation product of the PrP gene consists of 253 amino acids in humans (Kretzschmar, H. A. et al., *DNA* 5:315–324 (1986); Pucket, C. et al., *Am. J. Hum.* 49:320–329 (1991)), 254 in hamster and mice or 256 amino acids in sheep and undergoes several post-translational modifications. In hamsters, a signal peptide of 22 amino acids is cleaved at the N-terminus, 23 amino acids are removed from the C-terminus on addition of a glycosyl phosphatidylinositol (GPI) anchor, and asparagine-linked oligosaccharides are attached to residues 181 and 197 in a loop formed by a disulfide bond (Turk, E. et al., *Eur. J. Biochem.* 176:21–30 (1988); Hope, J. et al., *EMBO J.* 5:2591–2597 (1986); Stahl, N. et al., *Cell* 51:229–b 240 (1987); Stahl, N. et al., *Biochemistry* 29:5405–5412 (1990); Safar, J. et al., *Proc. Natl. Acad. Sci. USA* 87:6377 (1990)).

In prion-related encephalopathies, PrP$^c$ (normal cellular isoform) is converted into an altered form designated PrP$^{Sc}$, that can be experimentally distinguished from PrP$^c$ by the following three properties (Cohen et al. *Science* 264:530–531 (1994): (1) PrP$^{sc}$ is insoluble in physiological solvents and forms aggregates; (2) PrP$^{sc}$ is partially resistant to proteolytic degradation by proteinase K in that only the N-terminal 67 amino acids are removed by proteinase K digestion under conditions in which PrP$^c$ is completely degraded, and which results in a N-terminally truncated form known as PrP27-30; and (3) PrP$^{sc}$ has an alteration in protein conformation from α-helical for PrP$^c$ to an altered form which is rich in β-sheet secondary structure.

Several lines of evidence indicate that PrP$^{sc}$ is a major and necessary component of the infectious prion (reviewed in Prusiner, S. B. *Science* 252:1515–1522, 1991) and are as follows: (a) copurification of PrP27-30 and scrapie infectivity were determined by biochemical methods where the concentration of PrP27-30 is proportional to prion titer; (b) kinetics of proteolytic digestion of PrP27-30 and infectivity are similar; (c) copurification of PrP$^{sc}$ and infectivity were observed using immunoaffinity; (d) infectivity was neutralized by anti-PrP antibodies; (e) detection of PrP$^{sc}$ were only detected in clones of cultured cells producing infectivity; (f) most, if not all, of the familial cases of PrP-related disorders are linked to mutations in the PrP gene; (g) mice expressing PrP genes with point mutations linked to GSS spontaneously develop neurologic dysfunction, spongiform brain degeneration and astrocytic gliosis; (h) the species barrier to prion transmission from hamster to mouse could be overcome by introducing a Syriam hamster PrP transgene into the recipient mouse line; and (i) mice devoid of PrP gene are resistant to scrapie infection, developing neither symptoms of scrapie nor allowing propagation of the infectious agent. It has also been established that the protease-resistant core of PrP$^{sc}$ is the major structural protein of amyloid fibrils that accumulate intracerebrally in some of these conditions (Brendheim, P. E. et al., *Nature* 310:418–421 (1984); DeArmond, S. J. et al., *Cell* 41:221–235 (1985); Kitamoto, T. et al., *Ann. Neurol.* 20:204–208 (1986); Robert, G. W. et al., *N. Engl. Med.* 315:1231–1233 (1986); Ghetti, B. et al., *Neurology* 39:1453–1461 (1989); Tagliavini, F. et al., *EMBO J.* 10:513–519 (1991); Kitamoto, T. et al., *Neurology* 41:306–310 (1991)).

Although there are obvious differences in the etiology and pathogenesis of PrP-related diseases and Alzheimer's disease (AD), a remarkable number of similarities exist (for reviews, see Kelly, J. W. *Curr. Opin. Struct. Biol.* 6:11–17, 1996; Castano, E. M. & Frangione, B. *Curr. Opin. Neurol.* 8:279–285, 1995; Diringer, H. *Exp. Clin. Immunogenet.* 9:212–229, 1992; DeArmond, S. J. *Curr. Opin. Neurol.* 6:872–881, 1993), namely: (a) the clinical symptoms of both diseases are similar, including memory loss, behavioral abnormalities, cognitive problems and dementia; (b) both disorders are characterized clinically by age-related sporadic and familial forms of the disease; (c) an abnormal form of a neuronal membrane protein (Amyloid-β precursor protein and PrP) appears to play a key role in the pathogenesis of both diseases; (d) both Aβ and PrP are amyloidogenic and neurotoxic; (e) an important part of the cases affected by familial prion disease typically develop neuritic plaques similar to the AD plaques, but containing PrP (instead of Aβ) amyloid cores; (f) a hallmark event in both diseases is the conformational transition from an α-helical-random coil structure to a β-sheet conformation in either PrP or Aβ.

While amyloid deposition is not a general characteristic of PrP-related diseases, extensive evidence suggests that the disorder is caused by a disease-specific posttranslational modification of a normal protein isoform (cellular PrP or PrP$^c$) which results in the abnormal scrapie PrP (PrP$^{sc}$) (Prusiner, S. B. *Science* 252:1515–1522, 1991). Chemical differences have not been detected between the two PrP isoforms; they only differ in their conformations. For instance, the major secondary structure of PrP$^{sc}$ is β-ple-ated sheet, as opposed to the predominance of α-helix in PrP$^c$ (Pan, K. M. et al. *Proc. Natl. Acad. Sci. (USA)* 90:10962–10966, 1993). As discussed above, while amyloid or amyloid-like deposits are not observed in all subjects with a PrP-related disease, the pathological β-sheet-rich conformation of PrP$^{sc}$ as an abnormal precursor of amyloid or amyloid-like deposits however are always present.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention relates to novel inhibitory peptides capable of interacting or binding to a hydrophobic β-sheet forming cluster on a protein or peptide which forms amyloid or amyloid-like deposits so as to inhibit or structurally block the abnormal folding of the protein or peptide into a pathological β-sheet structure to form an amyloid or amyloid-like deposit, or a precursor thereof, such as is observed in Alzheimer's disease, amyloidosis disorders, prion-related encephalopathies, etc. The peptide includes a hydrophobic portion having one or more β-sheet blocking amino acid residues, and may also include charged amino acids at one or both ends of the peptide. Such inhibitory peptides have a low probability of adopting a β-sheet conformation and are capable of associating with said hydrophobic β-sheet forming cluster on the protein or peptide to structurally block and inhibit the abnormal folding thereof into amyloid or amyloid-like deposits, or pathological β-sheet precursors of amyloid or amyloid-like deposits.

The present invention also relates to a method of preventing or treating a disorder or disease associated with the formation of amyloid or amyloid-like deposits involving the abnormal folding of a protein or peptide having a hydrophobic β-sheet forming cluster into a β-sheet structure, by administering an effective amount of such an inhibitory peptide to a subject in need thereof to prevent or reverse the abnormal folding of the protein or peptide into amyloid or amyloid-like deposits or pathological β-sheet precursors thereof.

The present invention further relates to pharmaceutical compositions for the prevention or therapeutic treatment of disorders or diseases associated with abnormal protein folding into amyloid or amyloid-like deposits and pathological β-sheet-rich precursors thereof, using such inhibitory peptides.

The present invention also relates to a method for detecting disorders or diseases associated with amyloid or amyloid-like fibril deposits and pathological β-sheet-rich precursors thereof.

BRIEF DESCRIPTION OF THE DRAWINGS

FIG. 1A is the primary structure of the amyloidogenic sequence of peptides involved in the formation of several amyloid deposits. The sequences correspond to: amyloid β-peptide (SEQ ID NO: 1) found in Alzheimer's disease, its Dutch variant and Downs Syndrome; amyloid A (SEQ ID NO: 2) found in secondary amyloidosis and familial Mediterranean fever; gelsolin amyloid (SEQ ID NO: 3) related to familial amyloidosis of Finnish type; amyloid L (SEQ ID NO: 4) found in immunoglobulin-related primary amyloidosis; β2-microglobulin amyloid (SEQ ID NO: 5) found in patients with chronic hemodialysis-related amyloidosis; and apolipoprotein AI amyloid (SEQ ID NO: 6) related to familial amyloidotic polyneuropathy. Amino acids written in bold correspond to hydrophobic residues and those underlined represent positions with mutation related to the hereditary form of the disease. FIG. 1B provides the β-sheet prediction for the 15 amino acid fragments containing the sequences shown in FIG. 1A. The solid bar represents regions with a high probability of adopting a β-sheet structure.

FIG. 2A shows the amino acid sequences four anti-amyloid peptides labeled as anti-amyloid 1 (SEQ ID NO: 7), anti-amyloid 2 (SEQ ID NO: 8), anti-amyloid 3 (SEQ ID NO: 9) and anti-amyloid 4 (SEQ ID NO: 10). Hydro-phobic amino acids are highlighted in bold.

FIG. 2B shows the circular dichroism spectrum of the anti-amyloid peptide 1 (SEQ ID NO: 7) recorded as described in Example 1.

FIG. 4A shows the dose-dependent inhibition of amyloidogenesis, using anti-amyloid peptide 2 (shown as filled squares) and a 12 amino acid-non related peptide as a control (shown as unfilled square). The incubation time was 24 hours at room temperature and the Aβ concentration was 1 mg/ml in 0.1 M Tris, pH 7.4. FIG. 4B shows the effect of anti-amyloid peptide 2 (SEQ ID NO:8) on the amyloid formation after various incubation times. The inhibitory effect of the peptide remained unaltered over several days of incubation. Incubations containing Aβ, alone, are depicted by unfilled squares; incubations of Aβ, and a control peptide are depicted by unfilled circles; and incubations of Aβ and anti-amyloid peptide 2 are depicted by filled squares. The Aβ concentration used was 1 mg/ml incubated in a molar ratio of anti-amyloid peptide 2 or control peptide of 1:20. Neither the anti-amyloid peptide 2 nor the control peptide gave fluorescence values over the background level of 1-2 fluorescence units.

FIG. 5B) and anti-amyloid peptide 1 alone (FIG. 5C). Aliquots of Aβ were incubated at 1 mg/ml with or without the anti-amyloid peptide 1 in a molar ratio 1:50 (Aβ:anti-amyloid) for 6 days at room temperature.

FIGS. 6A–B show the effects of anti-amyloid peptide 1 on the redissolution of preformed fibrils. Amyloid fibrils were formed by incubating Aβ (1 mg/ml) for 3 days at room temperature. Anti-amyloid peptide 1 was then added in a molar ratio 1:50 (Aβ:anti-amyloid peptide 1). The incubation was continued for 15 minutes, 6 hours or 24 hours and the amyloid formation was quantitated by the fluorometric assay (FIG. 6A). Fluorescence values represent the amount of amyloid formed. FIG. 6B provides electron micrographs of the nonincubated (left side picture) and incubated fibrils for 24 hours with anti-amyloid peptide 1 (right side picture). Magnification is 50,000×.

FIGS. 7A–C show the physio-chemical characterization of the amphoterin (HMG-1) derived amyloid fragment, $ATN_p$. FIG. 7A provides the amino acid sequence of the fragment $ATN_p$ (SEQ ID NO: 11) Hydrophobic amino acid residues are highlighted in bold. FIG. 7B shows the Chou-Fasman prediction for β-sheet structure of $ATN_p$. The sequence with the highest β-sheet structure probability is indicated with a bar. FIG. 7C is an electron micrograph of negative-stained preparations of $ATN_p$ with formed amyloid-like fibrils.

FIG. 14A shows the effect of different molar ratios of iAβ or control peptide on fibril disassembly after 24 h of incubation. FIG. 14B fibril dissolution induced by a 40-fold molar excess of iAβ or control peptide after different incubation periods at room temperature.

FIG. 15a shows Aβ incubated for 6 days; FIG. 15b shows Aβ incubated with iAβ for 6 days; FIG. 15c shows Aβ incubated alone for 5 days and then for 1 day with iAβ; FIG. 15d shows iAβ incubated for 6 days at the same concentration as in FIGS. 15b and c; FIG. 15e shows Aβ incubated with the control peptide for 6 days; and FIG. 15f shows control peptide incubated alone for 6 days at the same concentration used in FIG. 15e.

FIGS. 23A and 23B show the effect of the presence (FIG. 23B) or absence (FIG. 23A) of peptide iPrP-12aa on PrP109-141 fibrillogenesis as evaluated by electron microscopy.

DETAILED DESCRIPTION OF THE PREFERRED EMBODIMENTS

Novel peptides specifically designed to interfere with the β-sheet conformation of precursor proteins or peptides involved in the formation of amyloid or amyloid-like deposits have been developed. The present invention is directed to these novel peptides, pharmaceutical compositions containing one or a mixture of such peptides of the invention, and methods for preventing, treating, or detecting disorders or diseases associated with abnormal protein folding into amyloid or amyloid-like deposits or precursors thereof having a pathological β-sheet structure.

Figures 1A, 1B:
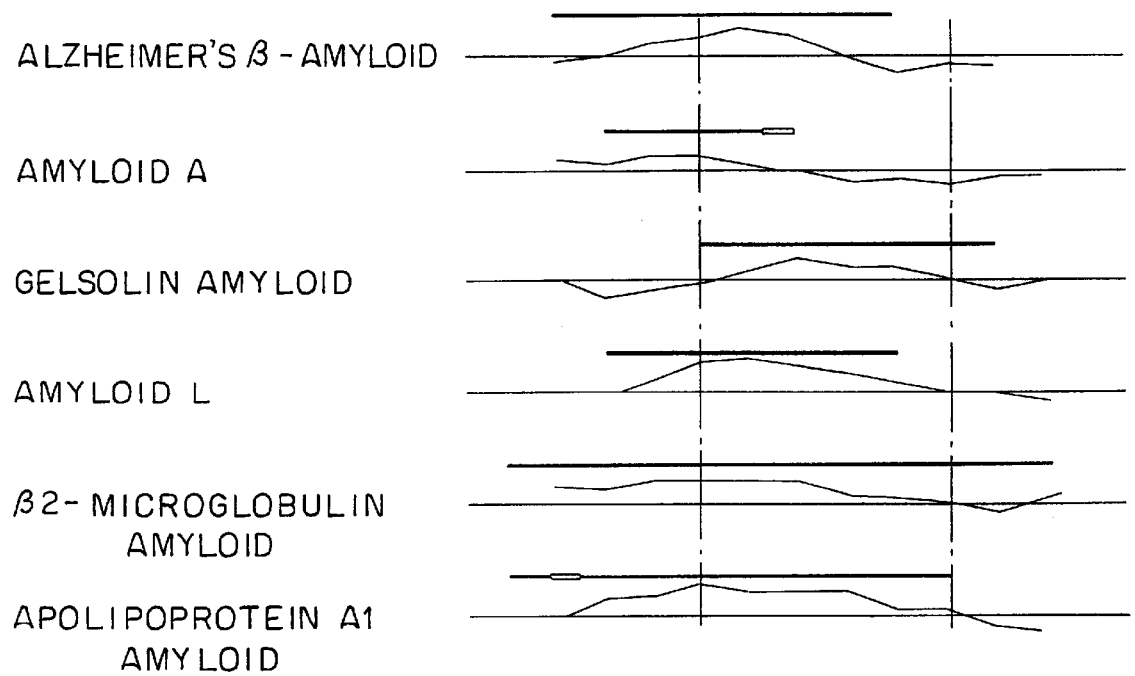
FIGS. 1A–B provide a consensus sequence for amyloidogenesis in terms of hydrophobicity and secondary structure properties.
Figure 3:
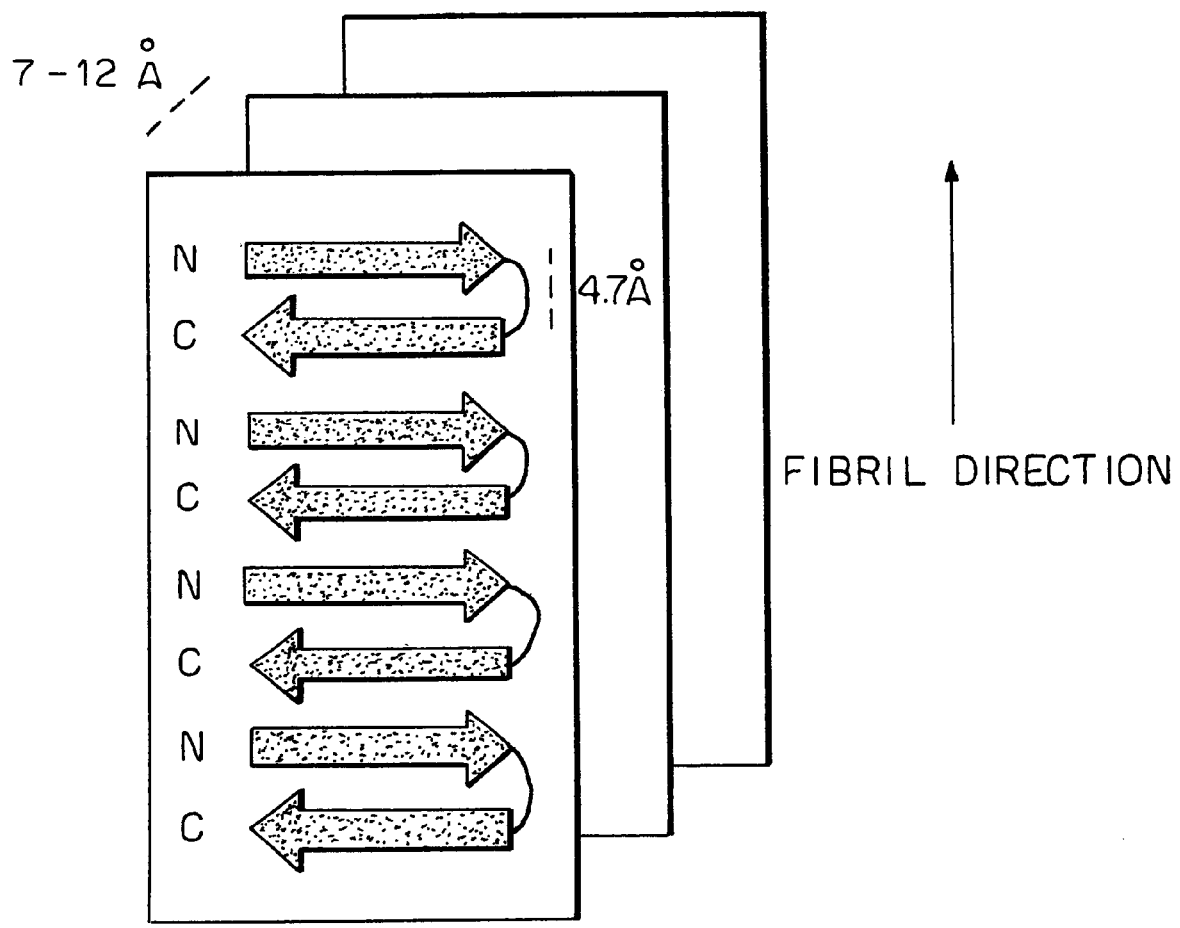
FIG. 3 is a schematic representation of the β-cross conformation for amyloid fibrils showing the crucial importance of the interactions by hydrogen bonding between the monomeric β-strand to form the intermolecular β-cross structure.
Figure 4A:
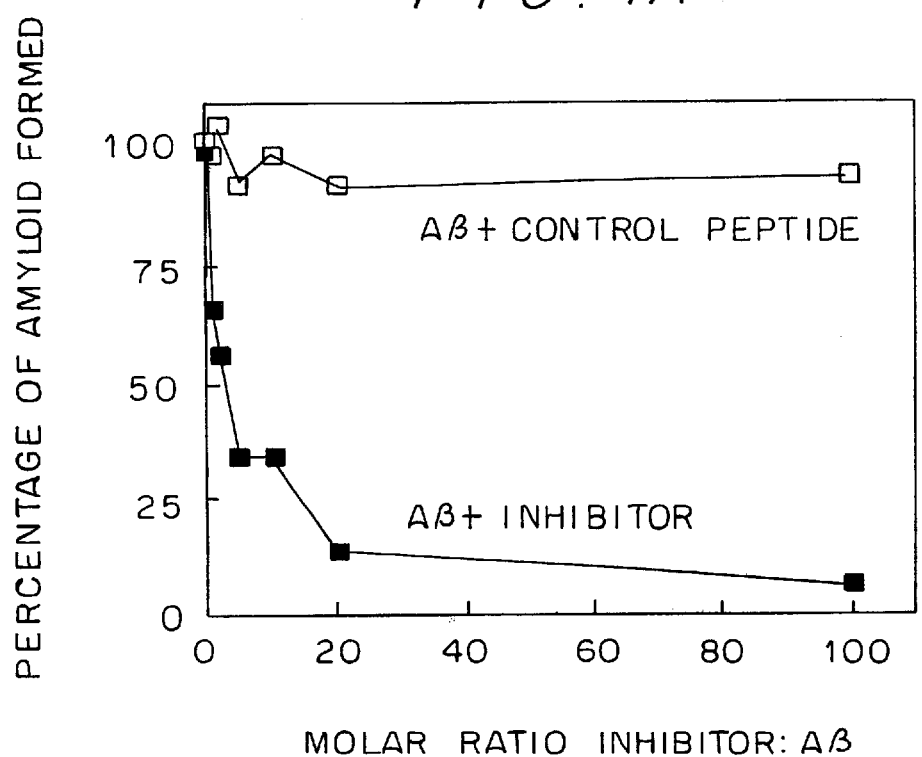
FIGS. 4A–B show the effect of anti-amyloid peptide 2 having the sequence of SEQ ID NO:8 on the amyloid formation by Aβ in vitro. Amyloid formation was quantitated by the fluorometric assay described in Example 1.
Figure 4B:
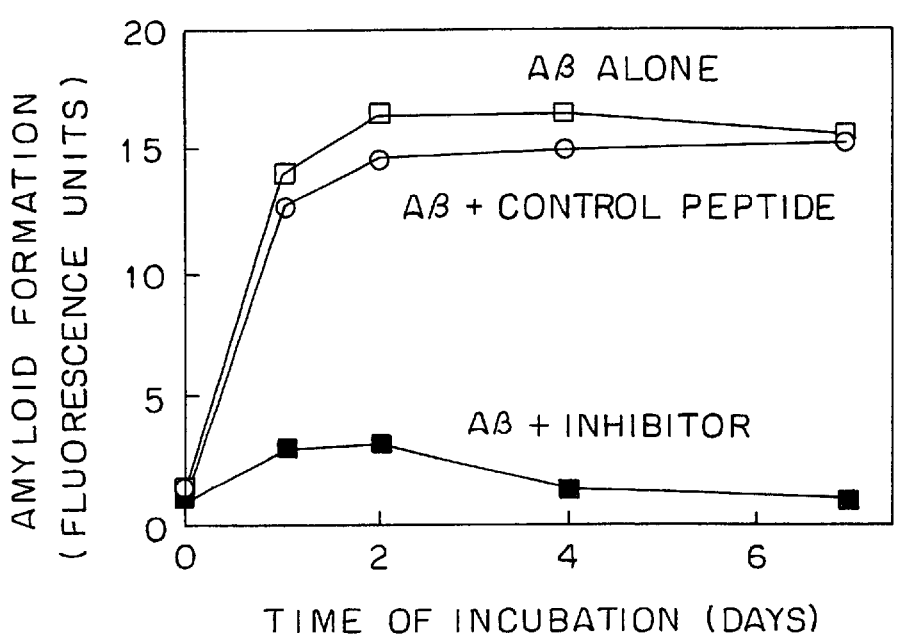
Figure 7C:
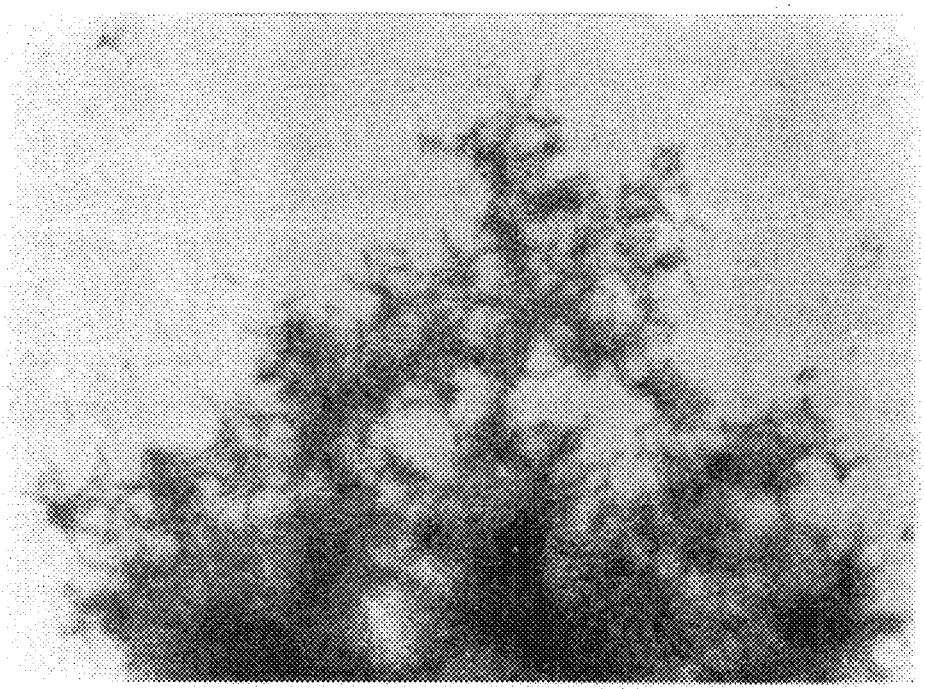

It has now been found that, while the amino acid sequence of proteins or peptides from different amyloid or amyloid-like deposits, or pathological precursors thereof, differ, all of these amyloidogenic proteins or peptides contain a segment having the common characteristic of a hydrophobic β-sheet forming cluster of amino acids (mainly phenylalanine, valine, alanine, leucine, and isoleucine) being present within a larger segment strongly predicted to have a β-sheet conformation (FIGS. 1A and 1B). The hydrophobic β-sheet forming cluster is believed to determine the binding of protein or peptide monomers resulting in aggregation, whereas the β-sheet potential of the longer sequence, of which the hydrophobic β-sheet forming cluster is a part, is believed to control the ordering of the aggregates into a β-cross conformation (β-cross quaternary fibril structure) typical of amyloid fibril structure (FIG. 3). Even a non-amyloid related peptide, which contains a potential amyloidogenic sequence motif (FIGS. 7A and 7B) such as obtained by proteolysis of amphoterin, forms typical amyloid-like fibrils in vitro (FIG. 7C).

The novel peptides of the present invention contain a hydrophobic portion or segment of at least three amino acid residues, where this portion is interrupted by one or more β-sheet blocking amino acid residues without substantially changing the hydrophobicity of the portion. In addition, these novel peptides can contain more than three hydrophobic amino acid residues within this portion, and/or contain other amino acid residues within this cluster or outside of it that also act to lower the propensity of the peptides of the present invention to adopt a β-sheet conformation.

Preferably, the peptides capable of interacting or binding with a structural determinant having a hydrophobic β-sheet forming cluster of amino acid residues on a protein or peptide involved in amyloid or amyloid-like deposit formation, which inhibits the abnormal folding of such a protein or peptide, are designed with a knowledge of the structural determinants for amyloid, amyloid-like deposits, or pathological β-sheet precursor formation by prediction of a hydrophobic β-sheet forming cluster and/or by experimental confirmation of β-sheet conformation. However, prior identification of the structural determinant is not always necessary.

Peptides having a hydrophobic β-sheet blocking portion which interacts with a hydrophobic β-sheet forming determinant of the protein or peptide, but with a very-low probability of adopting a β-sheet conformation themselves, are designed to bind to the structural determinant and to function as an inhibitor of the conformational change resulting in the pathological β-sheet rich precursors of amyloid fibril formation and/or as an agent that dissolves preformed amyloid fibrils. In addition, one or more charged amino acid residue, such as aspartic acid, glutamic acid, arginine, or lysine, can be placed at one or both ends of the peptide to increase the solubility of the inhibitory peptide.

Furthermore, the inhibitory peptides of the invention contain one or more β-sheet blocking amino acids, such as Pro, Gly, Asn, or His, either within the hydrophobic portion containing at least three amino acid residues or immediately adjacent to this portion so as to prevent the binding of protein or peptide monomers into aggregates and the ordering of such aggregates into an altered conformation such as the β-cross conformation typical of amyloid fibril structure. While the peptides can be designed to be preferably homologous or partially homologous to the hydrophobic β-sheet forming cluster as the structural determinant they are to interact with, amino acid homology is not absolutely required as long as the peptide has a portion of sufficient hydrophobicity so that it will interact strongly with the hydrophobic β-sheet forming cluster to structurally block abnormal protein or peptide folding into fibril deposits or pathological β-sheet-rich precursors thereof.

In the design of the inhibitory peptides of the present invention, it is important not only to have a hydrophobic portion or cluster that can interact and bind to the hydrophobic β-sheet forming cluster of the amyloidogenic protein or peptide, but also to introduce one or more β-sheet blocking amino acid residues. Thus, whereas the hydrophobicity of the inhibitory peptide facilitates the binding interaction with the amyloidogenic protein or peptide, the presence of one or more β-sheet blocking amino acid residues, located in the hydrophobic portion or immediately adjacent to it, lowers the β-sheet forming potential of the inhibitory peptide and inhibits the conformational transition of the amyloidogenic protein or peptide into a β-sheet structure found to be formed in amyloid or amyloid-like deposits and pathological β-sheet precursors thereof.

As a general non-limiting example of a preferred design approach, which was used for some of the inhibitory peptides of the present invention (such as some of the peptides of Table 1), a peptide is designed so that a hydrophobic portion of at least three amino acids is homologous to the hydrophobic β-sheet forming cluster predicted or identified experimentally to be involved in abnormal protein folding into a β-sheet structure. Highly hydrophobic amino acid residues of the hydrophobic β-sheet forming cluster are generally incorporated into the sequence of the homologous hydrophobic portion of the inhibitory peptide. In addition, any non-hydrophobic or poorly hydrophobic amino acid residues in the hydrophobic β-sheet forming cluster can be incorporated into the homologous hydrophobic portion, or deleted, or replaced with another amino acid such as a β-sheet blocking residue, preferably proline.

It is intended that the homologous hydrophobic portion of the inhibitory peptide has one or more β-sheet blocking residues that interrupt the homology to the hydrophobic β-sheet forming cluster by avoiding the presence of more than three contiguous amino acids within the homologous hydrophobic portion which are 100% homologous to the corresponding contiguous amino acids in the hydrophobic β-sheet forming cluster. In this manner, the propensity or potential for forming a β-sheet conformation is dramatically reduced for the hydrophobic portion and for the inhibitory peptide as a whole, while the degree of hydrophobicity of the hydrophobic portion is kept substantially unchanged from that of the hydrophobic β-sheet forming cluster. This provides for the capability of the inhibitory peptide to hydrophobically interact/bind with the amyloidogenic protein or peptide where the β-sheet blocking capability of the designed inhibitory peptide is allowed to manifest itself by inhibiting the formation of β-sheet structures characteristic of amyloid or amyloid-like deposits and precursors thereof.

An additional design parameter that is to be considered is the addition of charged amino acid residues at one or both ends of the inhibitory peptide which act mainly to increase the solubility of the peptide in an aqueous medium. This feature is more important with longer peptides and while preferred, is not absolutely necessary in short peptides.

It will be appreciated that those of skill in the art can easily synthesize an array of inhibitory peptides, designed in accordance with the present invention, that can be readily tested using the methods described in Examples 1 and 2 for Aβ and PrP, respectively, for the ability to inhibit the conformational transition of amyloidogenic proteins or peptides into pathological β-sheet structures as precursors to, or as fibrils of, amyloid or amyloid-like deposits.

Prion protein PrP normally assumes an α-helical conformation, but abnormal protein folding alters the normal PrP conformation to an abnormal β-sheet conformation. Considering the similarities between PrP-related disorders and Alzheimer's disease, and since the acquisition of a β-sheet structure plays a crucial role in the disease, inhibitor peptides are designed to bind to PrP to prevent abnormal protein folding into an altered conformation that would result in amyloid or amyloid-like deposits or pathological β-sheet precursors thereof, and thus can be used in the treatment of PrP diseases.

Non-limiting examples of peptides designed to inhibit abnormal folding in the formation of amyloid and amyloid-like deposits, or pathological β-sheet precursors thereof are presented in Table 1. The anti-PrP peptides are designed to bind to the hydrophobic β-sheet forming structural determinant of PrP corresponding to amino acid residues 114 to 125 of prion (presented as SEQ ID NO:23). While Pro is used as the preferred β-sheet blocking amino acid in virtually all the peptides presented in Table 1, other β-sheet blockers, such as Gly (exemplified in the peptide of SEQ ID NO:48), Asn and His, are suitable. The peptides of Wood et al., 1995, supra, having the amino acid sequences of SEQ ID NOs:50–65 are specifically excluded from the peptides of the present invention.

TABLE 1

Examples of Peptides Inhibiting Abnormal Protein Folding

1. Anti-amyloid peptides
SEQ ID NO:7
SEQ ID NO:8 (iAβ)
SEQ ID NO:9
SEQ ID NO:10
    a) shorter derivatives of iAβ (SEQ ID NO:8)
        SEQ ID NO:15
        SEQ ID NO:16
        SEQ ID NO:17
        SEQ ID NO:18
        SEQ ID NO:19
        Pro-Phe-Phe
        SEQ ID NO:27
        SEQ ID NO:28
        SEQ ID NO:29
        SEQ ID NO:30
        SEQ ID NO:31
        SEQ ID NO:32
        SEQ ID NO:33
        SEQ ID NO:49
    b) derivatives of iAβ with higher hydrophobicity
        SEQ ID NO:20
        SEQ ID NO:21
        SEQ ID NO:22
2. Anti-prion (PrP) peptides
SEQ ID NO:24
SEQ ID NO:25
SEQ ID NO:38
SEQ ID NO:39
SEQ ID NO:40
SEQ ID NO:41
SEQ ID NO:42
SEQ ID NO:43
SEQ ID NO:44
SEQ ID NO:45
SEQ ID NO:46
SEQ ID NO:47

Methods for predicting protein conformation to aid in the design of peptide that have a hydrophobic portion and a low probability of abnormally folding into an altered conformation such as a β-sheet are described in Chou and Fasman, *Ann. Rev. Biochemn.* 47:251–276, 1978, Garnier et al., *J. Mol. Biol.* 120:97–120, 1978, and Minor et al. *Nature* 371:264–267, 1994.

A specific non-limiting example of the general preferred design approach described above for designing Aβ inhibitory peptides according to the present invention first identifies the hydrophobic β-sheet forming cluster of Aβ, Leu Val Phe Phe Ala (corresponding to residues 2–6 of SEQ ID NO:1). The alanine residue which is poorly hydrophobic, can be replaced with the preferred β-sheet blocker, proline, or can be deleted altogether. The Aβ inhibitory peptide in Table 1 having the sequence of SEQ ID NO:18 is designed to be homologous to amino acid residues 2–6 of SEQ ID NO:1 where a proline β-sheet blocking residue is substituted for the valine residue, and a charged aspartic acid residue is placed at the end of the peptide. This peptide has a β-sheet blocker interrupting the hydrophobic β-sheet forming cluster of Aβ such that there are no more than three contiguous amino acids corresponding to the hydrophobic β-sheet forming cluster in the hydrophobic portion of the Aβinhibitory peptide. Not only does the Aβinhibitory peptide of SEQ ID NO:18 have a low β-sheet forming potential, but it also substantially retains the hydrophobicity of the hydrophobic β-sheet forming cluster corresponding to residues 2–6 of SEQ ID NO:1. The charged aspartic acid residue at the end improves the solubility of the peptide. Instead of replacing the valine residue, proline can be designed to replace one of the phenylalanine residues to yield Aβinhibitory peptides having the sequences of SEQ ID NOs:27and 28. Another possibile design to insert a valine into the sequence of SEQ ID NO:18 to arrive at an inhibitory peptide having the sequence of SEQ ID NO:17.

It will be appreciated by those in the art that besides the twenty common naturally occurring amino acids, modified amino acids or naturally occurring but rare amino acids can also be incorporated into the peptides of the present invention. For instance, it was demonstrated that a peptide with amino acid residues in the D-form inhibited fibrillogenesis of Aβ just as well as the peptide with the same sequence of amino acids in the L-form (see Example 1). It will also be appreciated by those of skill in the art that the peptides of the present invention are intended to include pseudo-peptides, semi-peptides, peptoids and peptide mimetics (Kessler, *Angew. Chem. Int. Ed.* 32:543–544, 1993, Moore, *TIPS* 15:124–129, 1994) which provide the characteristics of a cluster or portion of at least three hydrophobic residues and one or more β-sheet blockers interrupting this cluster or portion and/or located immediately adjacent to it, so as to have a low probability of forming a β-sheet or β-sheet-like conformation, and thereby inhibiting aggregation/formation of amyloid or amyloid-like deposits or the precursors thereof.

Modifications to amino acids in the peptides of the invention include, but are not limited to, an amide moiety or a pyroglutamyl residue. These modifications may contribute to decreasing the propensity to form β-sheet conformation or may contribute to peptide stability, solubility, or even immunogenicity. A more stable, soluble and less immunogenic peptide is desirable. Many neuropeptides modified at the C-terminus with a $CONH_2$ (amide) group appear to be resistant to attack by carboxypeptidases and many neuropeptides having a pyroglutamyl residue at the N-terminus are more resistant to attack by broad specificity amino peptides. Also included as peptides of the present invention are cyclic peptides that are resistant to attack by both carboxypeptidases and aminopeptidases.

As a method of preventing or treating a disorder or disease associated with amyloid or amyloid-like deposits and pathological β-sheet-rich precursors thereof, the inhibitory peptide of the present invention is administered in an effective amount to a subject in need thereof, where the subject can be human or animal. Likewise, a method of detecting such disorders or diseases also includes administering a sufficient amount of the designed peptide to visualize its binding to fibril deposits or precursors thereof by well-known imaging techniques. To facilitate the transport of the peptides of the present invention across the blood-brain barrier, peptides inhibitory to the formation of amyloid deposits in Alzheimer's disease can be preferably complexed with apolipoprotein J, as described in Zlokovic et al., *Biochem. Biophys. Res. Commun.* 205:1431–1437, (1994) and *Proc. Natl. Acad. Sci. USA* 93:4229–4234 (1996). Apolipoprotein J is believed to be a normal carrier for transport of Aβ into the brain parenchyma. The laboratory of the present inventors has found that the region responsible for interacting with apolipoprotein J in Aβ is the sequence corresponding to residues 17–25 of Aβ (SEQ ID NO:1). Since this sequence is used as a template for the design of Aβ inhibitor peptides, these inhibitor peptides are expected to also be capable of interacting with apolipoprotein J and be transported across the blood-brain barrier using the receptor for apoJ.

As used herein, the term "prevention" of a condition, such as Alzheimer's disease or other amyloidosis disorders, in a subject involves administering a peptide according to the present invention prior to the clinical onset of the disease. "Treatment" involves administration of the protective peptide after the clinical onset of the disease. For example, successful administration of the peptide of the present invention, after development of a disorder or disease comprises "treatment" of the disease. The invention is useful in the treatment of humans as well as for veterinary uses in animals.

The peptides of the present invention may be administered by any means that achieves its intended purpose. For example, administration may be by a number of different parenteral routes including, but not limited to, subcutaneous, intravenous, intradermal, intramuscular, intraperitoneal, intracerebral, intranasal, oral, transdermal, or buccal routes. Parenteral administration can be bolus injection or by gradual perfusion over time.

A typical regimen for preventing, suppressing, or treating a condition associated with amyloid or amyloid-like deposits, comprises either (1) administration of an effective amount in one or two doses of a high concentration of inhibitory peptides in the range of 0.5 to 10 mg of peptide, more preferably 0.5 to 5 mg of peptide, or (2) administration of an effective amount of the peptide administered in multiple doses of lower concentrations of inhibitor peptides in the range of 10–1000 µg, more preferably 50–500 µg over a period of time up to and including several months to several years.

It is understood that the dosage administered will be dependent upon the age, sex, health, and weight of the recipient, kind of concurrent treatment, if any, frequency of treatment, and the nature of the effect desired. The total dose required for each treatment may be administered by multiple doses or in a single dose. By "effective amount", it is meant a concentration of inhibitor peptide(s) which is capable of slowing down or inhibiting the formation of amyloid or amyloid-like deposits, or pathological β-sheet precursors thereof, or of dissolving preformed fibril deposits. Such concentrations can be routinely determined by those of skill in the art. It will also be appreciated by those of skill in the art that the dosage may be dependent on the stability of the administered peptide. A less stable peptide may require administration in multiple doses.

Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

Pharmaceutical compositions comprising the peptides of the invention include all compositions wherein the peptide (s) are contained in an amount effective to achieve its intended purpose. In addition, the pharmaceutical compositions may contain suitable pharmaceutically acceptable carriers comprising excipients and auxiliaries which facilitate processing of the active compounds into preparations which can be used pharmaceutically. Suitable pharmaceutically acceptable vehicles are well known in the art and are described for example in Gennaro, Alfonso, Ed., Remington's Pharmaceutical Sciences, 18th Edition 1990, Mack Publishing Co., Easton, Pa., a standard reference text in this field. Pharmaceutically acceptable vehicles can be routinely selected in accordance with the mode of administration and the solubility and stability of the peptides. For example, formulations for intravenous administration may include sterile aqueous solutions which may also contain buffers, diluents and other suitable additives.

Suitable formulations for parenteral administration include aqueous solutions of the active compounds in water-soluble form, for example, water-soluble salts. In addition, suspension of the active compound as appropriate oily injections suspensions may be administered. Suitable lipophilic solvents or vehicles include fatty oils, for example, sesame oil, or synthetic fatty acid ester,s for example ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

Disorders or diseases associated with abnormal protein folding into amyloid or amyloid-like deposits or into pathological β-sheet-rich precursors of such deposits to be treated or prevented by administering the pharmaceutical composition of the invention includes, but is not limited to, Alzheimer's disease, FAF, Down's syndrome, other amyloidosis disorders, human prion diseases, such as kuru, Creutzfeldt-Jakob Disease .(CJD), Gerstmann-Straussler-Scheinker Syndrome (GSS), prion associated human neurodegenerative diseases as well as animal prion diseases such as scrapie, spongiform encephalopathy, transmissible mink encephalopathy and chronic wasting disease of mule deer and elk.

Besides preventative and therapeutic treatments, the peptides of the invention may also be administered to detect and diagnose the presence or absence of amyloid or amyloid-like deposits in vivo and precursors thereof. A designed peptide capable of binding to a hydrophobic β-sheet forming cluster as a structural determinant in a corresponding amyloid or amyloid-like deposit and precursors thereof, labeled non-radioactively or with a radioisotope, as is well-known in the art, can be administered to a subject for diagnosing the onset or presence of a disease or disorder associated with abnormal protein folding into amyloid or amyloid-like fibril deposits and pathological β-sheet-rich precursors thereof. The binding of such a labeled peptide after administration to amyloid or amyloid-like deposits or precursors thereof can be detected by in vivo imaging techniques known in the art.

Having now generally described the invention, the same will be more readily understood through reference to the following example which is provided by way of illustration and is not intended to be limiting of the present invention.

EXAMPLE 1

Amyloid deposition appears to be an important factor in the development of neuritic plaque and neuronal disfunction in AD. The results of the study presented below indicate that a short peptide partially homologous to the central hydrophobic region of Aβ (residues 17–21), but containing amino acids which block the adoption of a β-sheet structure binds Aβ, inhibits amyloid formation in vitro and dissolves preformed Aβ fibrils. Furthermore, the inhibitor is able to block the in vivo deposition of AA in the spleen of mice.

Since the inhibition of fibrillogenesis and the disassembly of preformed fibrils occurs in the presence of a molar excess of an 11 amino acid peptide, called inhibitor of Aβ fibrillogenesis peptide (iAβ) and also designated as anti-amyloid peptide 2, the Aβ-Aβ interaction probably has a greater affinity than the Aβ-iAβ interaction. Although a molar excess of iAβ is required to produce the inhibition of amyloid formation, the very low concentration of sAβ present in human body fluids (1–10 nM) would necessitate only 40–400 nM of iAβ for a 40-fold molar excess.

The results of the study support the concept that the formation of a β-sheet secondary structure is important for fibrillogenesis and it is believed that iAβ inhibits amyloid formation by binding to monomeric Aβ peptides thereby blocking the formation of the oligomeric β-sheet conformation precursor of the fibrils. The dissolution of preformed fibrils induced by iAβ may indicate that the monomeric peptide is in equilibrium with the fibrils, as previously suggested (Maggio, J. et al., *Proc. Natl. Acad. Sci. USA* 89:5461–5466, 1992; Tamaokoa, A. et al., *Biochem. Biophys. Res. Commun.* 205:834–842, 1994). The inhibitor may bind to monomeric peptide, thus displacing the equilibrium, and leading to fibril disaggregation.

Material and Methods

Peptide synthesis. Synthetic peptides containing the sequence 1–40, 1–42 of Aβ and the anti-amyloid peptides were synthesized by a solid phase technique on a p-methylbenzhydrylamine resin using a Biosearch SAM 2 synthesizer. Peptides were subjected to purification by high performance liquid chromatography (HPLC) with the use of a reverse-phase support medium (Delta-Bondapak) on a 0.78× 30 cm column with a 0–80% linear gradient of acetonitrile in 0.1% (v/v) trifluoroacetic acid. The peptide content of the eluate was monitored by measurement of its absorption at 220 nm. Peptide sequences were determined by automatic Edman degradation on a 477A protein sequencer and the PTH derivatives analyzed with an on-line 120 A PTH analyzer (Applied Biosystems, Foster City, Calif.). Purity of the peptides was evaluated by peptide sequencing and laser desorption mass spectrometry. Stock solutions of the peptides were prepared by dissolving them in 50% acetonitrile. The concentration was determined by amino acid composition analysis on a Waters Pico-Tag amino acid analyzer (Millipore Corp, Bedford, Mass.), after hydrolyzing the samples under reduced pressure-in the presence of 6M HCl for 20 hours at 110° C. For experiments, peptide aliquots were lyophilized and resuspended in the buffer used in the assay.

Prediction of Secondary Structure. The α-helix, β-sheet and β-turn propensities for different sequences were calculated by the Chou and Fasman secondary structure prediction algorithm (Chou and Fasman, *Ann. Rev. Biochem.* 47: 251–2760, 1978) using the program Protylze version 3.01 from Copyright.

Fluorimetric determination of amyloid formation. Aliquots of peptides were incubated for varying amounts of time at room temperature in 0.1 M Tris-HCl, pH 7.4. To quantitate amyloid formation, a thioflavine T (Tht) fluorescence method was used. Tht binds specifically to amyloid and this binding procedure produces a shift in its emission spectrum and a fluorescent signal proportional to the amount of amyloid formed (Naiki et al., Lab. Invest. 65:104–110, 1991). Thus, this method is very specific for the semiquantitation of amyloid-like aggregates. After incubation Aβ peptides were added to 50 mM glycine, pH 9.2, 2 μM Tht in a final volume of 2 ml. Fluorescence was measured at an excitation wavelength of 435 nm and an emission wavelength of 485 nm using a Hitachi F-2000 fluorescence spectrometer (Hitachi Instruments Inc., San Jose, Calif.). A time scan of fluorescence was performed and three values after the decay reached the plateau (280, 290 and 300 seconds) were averaged after subtracting the background fluorescence of 2 μM Tht.

Electron microscopy. For fibril formation, peptides (1 mg/ml) were incubated in 0.1 M Tris-HCl, pH 7.4, for 6 days at room temperature. Samples to be visualized were placed on carbon formvar-coated 300-mesh nickel grids for 1 minute, blotted and stained for 1 minute with 2% uranyl acetate under a vapor of 2% glutaraldehyde and visualized on a Zeiss EM 10 electron microscope (Carl Zeiss, Inc., Thornwood, N.Y.) at 80 kV.

Circular dichroism studies. The secondary structure of Aβ and inhibitor peptides was analyzed by circular dichroism in aqueous solution. Spectra were recorded in a Jasco spectropolarimeter Model J-720 (Jasco Inc., Easton, Md.). Aliquots of peptides at a concentration of 0.1–0.2 mg/ml in 20 mM Tris-HCl, pH 7.4, were first centrifuged to produce a clear solution and the spectra were recorded at 1 nm intervals over the wavelength range 190 to 260 nm in a 0.1 cm pathlength cell. Results are expressed in terms of mean residue ellipticity in units of deg $cm^2 dmol^{-1}$.

Binding sites. The interaction between Aβ an iAβP was studied by fluorescence spectroscopy at 25° C. using a Perkin Elmer model LS50B spectrofluorimeter. 45 μg of Aβ1-40 was dissolved in 300 μl of 5 mM Tris, pH 7.4 and immediately the fluorescence spectra was recorded between 290 nm an 400 nm at excitation 280nm; with slits set at 2.5nm bandwidth. Different amounts of lyophilized iAβ were added to the Aβ solution and after 15 min of incubation the fluorescence spectra was recorded, iAβ at the same concentrations did not give any fluorescence signal above the background. The binding of iAβ to Aβ was evaluated by the change in fluorescence intensity at 309 nm between the spectra of Aβ alone and in the presence of different concentrations of the inhibitor. The binding data were analyzed with the aid of a curve fitting software (GraphPad Prism version 1.0).

In vivo studies using the experimental murine model of amyloidosis. Induction of experimental amyloidosis was done as previously described (Merlini et al., *Proc. Natl. Acad. Sci. USA* 92:2959–2964, 1995; Snow et al., *J. Histochem. Cytochem.* 39:1321–1330, 1991). BALB/c mice were injected t.v. with 100 μg of amyloid enhancing factor (AEF) alone or preincubated for 24 h with 5 mg of iAβ. AEF was prepared using the standard protocols. The AEF injection was followed by a single s.c. injection of 0.5 ml of 2% silver nitrate. Animals were sacrificed 5 days after the injection and the amyloid quantitated by immunohistochemistry and congo red staining. A standard set of amyloid containing tissue was generated (5%, 10%, 20%, 30%, 40%, 50%). These were reference points to determine the amount of amyloid in a given tissue. Standard sections were examined under the microscope (Nikon, using polarizing filters to generate birefringence for Congo red). The images were digitized and transferred to a MacIntosh computer for analysis. The digitized images were analyzed for color (intensity and area) under low power (20×) using a Kontron or Prism Image Analysis. Experimental spleen tissue sections were fixed in 10% buffered formalin and embedded in paraffin and stained with antibodies against SAA. The experimental sections were analyzed and compared to the standards for quantitation of the area spleen containing amyloid. The experiments were performed using four animals per condition.

RESULTS

Figures 2A, 2B:
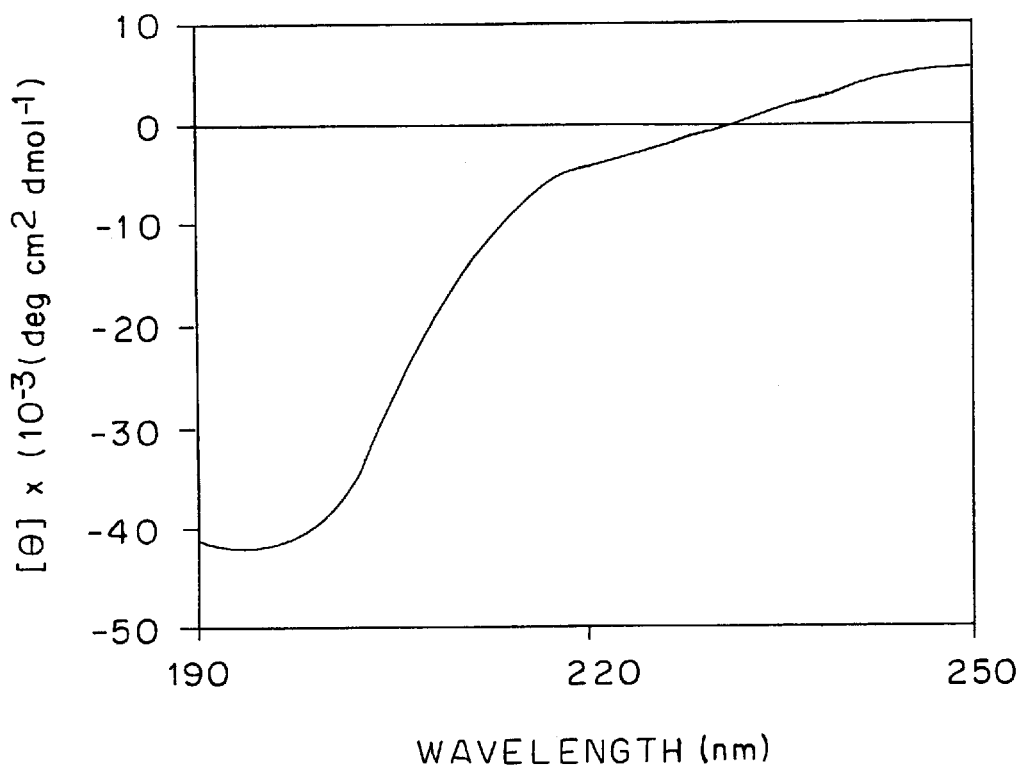
FIGS. 2A–B provide the amino acid sequence for several anti-amyloid peptides.
Figure 9:
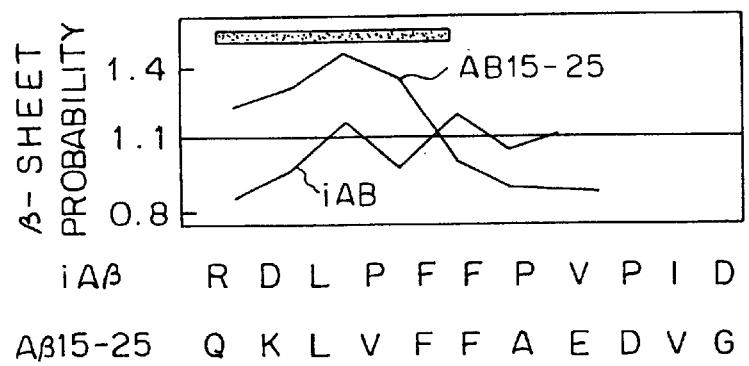
FIG. 9 shows the structural characteristics of anti-amyloid peptide 2(iAβ). The amino acid sequence and β-sheet probability for iAβ (SEQ ID NO:8) and for the region of Aβ (SEQ ID NO:14) used as a template for iAβ is shown underneath the β-sheet probability profile where the solid bar represents the region of Aβ having a high probability of β-sheet structure.

Design of inhibitor peptides. The laboratory of the present inventors focused on the central hydrophobic region within the N-terminal domain of Aβ, amino acids 17–21 (corresponding to amino acid residues 2–6 of SEQ ID NO:1), as a model for the inhibitor peptide (FIGS. 2A and 9). Proline residues were introduced in the inhibitor peptide in order to block β-sheet structure and charged residues were added at the ends of the peptide to increase solubility. Proline was chosen to block β-sheet structure since it rarely forms part of this conformation (Chou et al., *Ann. Rev. Biochem.* 47:251–276, 1978) and does not occur in the interior of antiparallel β-sheets (Wouters et al., *Protein Sci.* 3:43S, 1994), due to the extraordinary characteristics of this amino acid, namely: (a) the nitrogen of the peptide bond is not available to the β-sheet bonding network; (b) the torsion angles of the peptidyl-propyl bond imposed by the proline ring are incompatible with peptide bond geometries found in β-sheet motifs; and (c) the proline ring can not fit sterically within the β-sheet bonding network. Moreover, recent data showed that the introduction of proline residues into short peptides homologous to Aβ resulted in non-amyloidogenic analogues (Wood et al., *Biochem.* 34:724–730, 1995).

Figure 10:
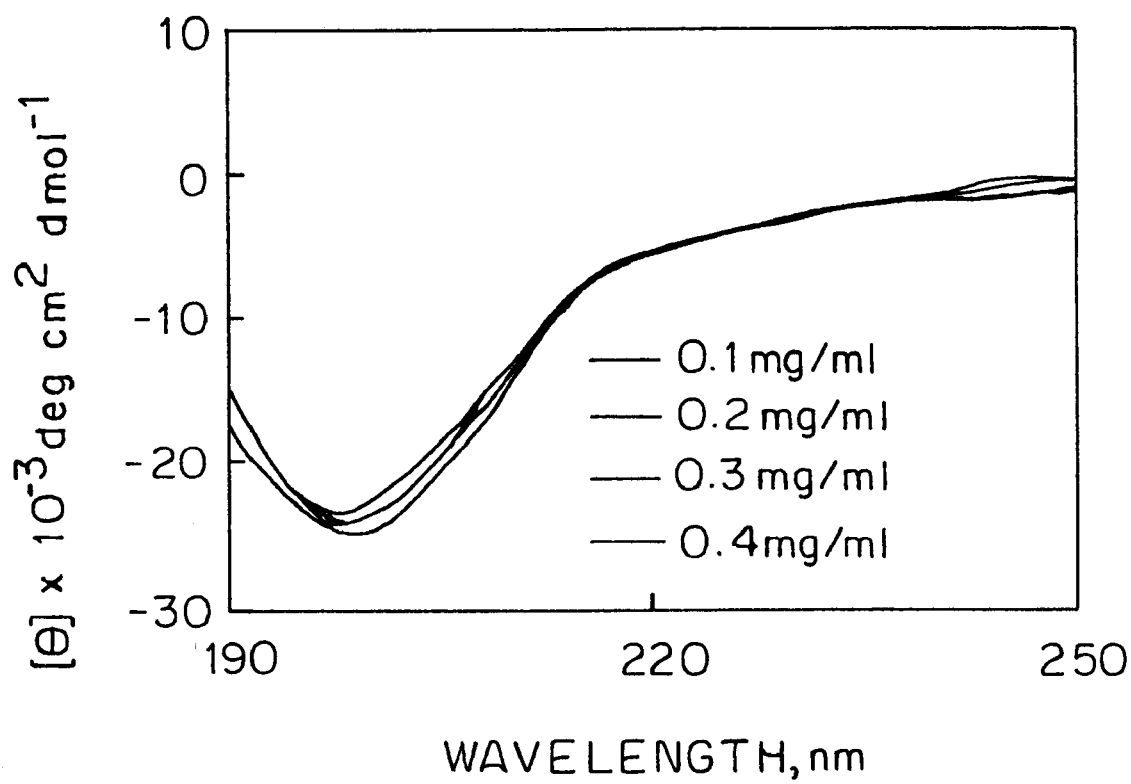
FIG. 10 shows the circular dichroism spectra of iAβ at different peptide concentration.

Based on these criteria, an 11 amino acid peptide, called inhibitor of Aβ fibrillogenesis peptide (iAβ) was designed, which has a low probability of adopting a β-sheet conformation due to the presence of proline residues (FIG. 9). Other peptide inhibitors based on the above criteria are shown in FIG. 2A. The circular dichroism spectrum of iAβ in aqueous solution was typical of unordered structures (FIG. 10). Samples of iAβ at different concentrations as well as samples incubated for several days have similar spectra (FIG. 10). Indeed, iAβ did not aggregate even at high concentrations (4 mg/ml) or after long periods of incubation (more than 30 days).

Figure 11A:
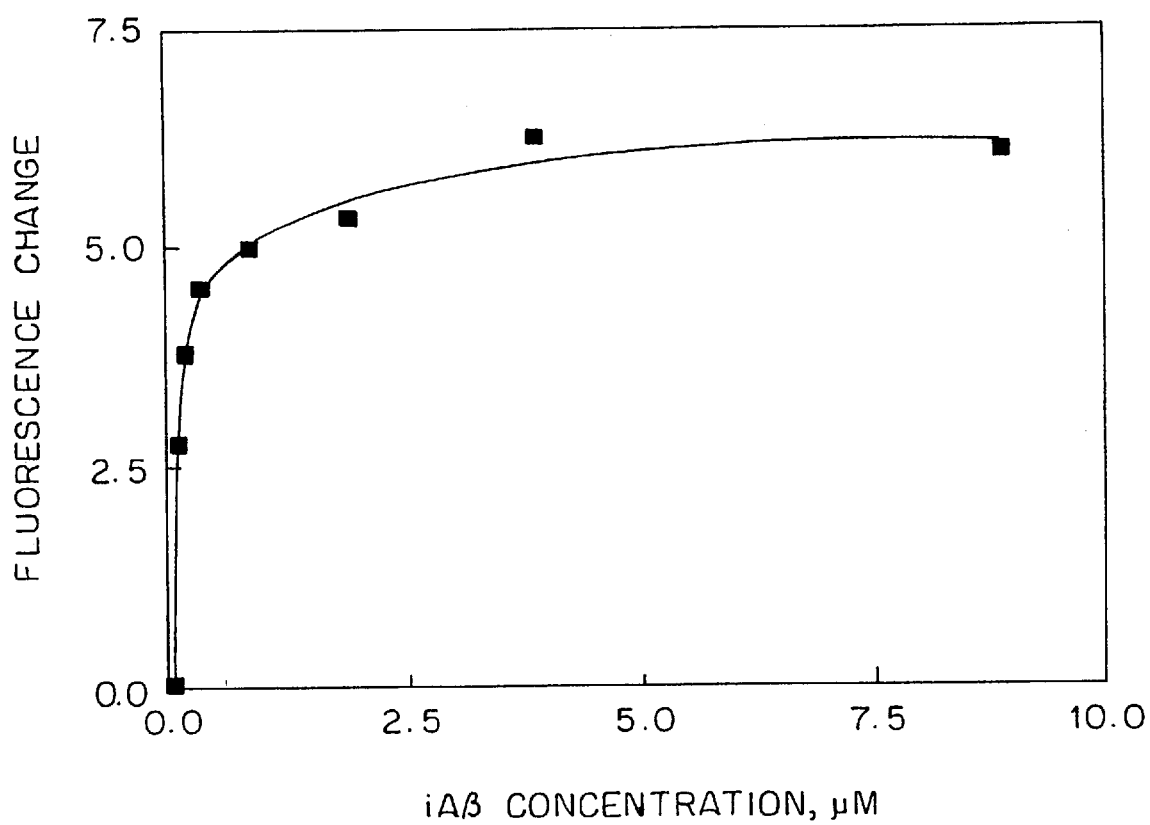
FIG. 11 shows the Aβ-iAβ interaction as quantitated by the quenching of the intrinsic fluorescence of Aβ (tyrosine 10) induced by the binding of iAβ. The inset shows the fluorescence spectra of Aβ incubated alone or in the presence of 4 μM iAβ.
Figure 11B:
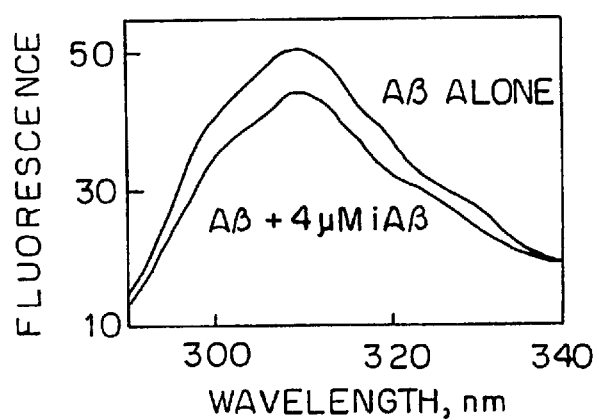

The interaction between Aβ and iAβ was studied by monitoring the quenching of Tyr[10] fluorescence of Aβ (FIG. 11). Fluorescence spectroscopy was chosen to study the interaction of Aβ- iAβ because this technique has been used extensively for ligand-binding studies and does not require peptide labelling with reagents that may alter their properties. Aβ excited at 280 nm showed a fluorescence spectrum with a maximum at 309 nm (FIG. 11, inset), which is typical of tyrosine emission. The presence of iAβ induced a saturable quenching of the fluorescence, reaching a maximum of 12.6% of the total fluorescence at approximately 4 µM of iAβ (FIG. 11). Non-linear regression analysis of the binding data to a rectangular hyperbola allowed calculation of a relative dissociation constant of 75.9±6.5 nM.

Figure 12:
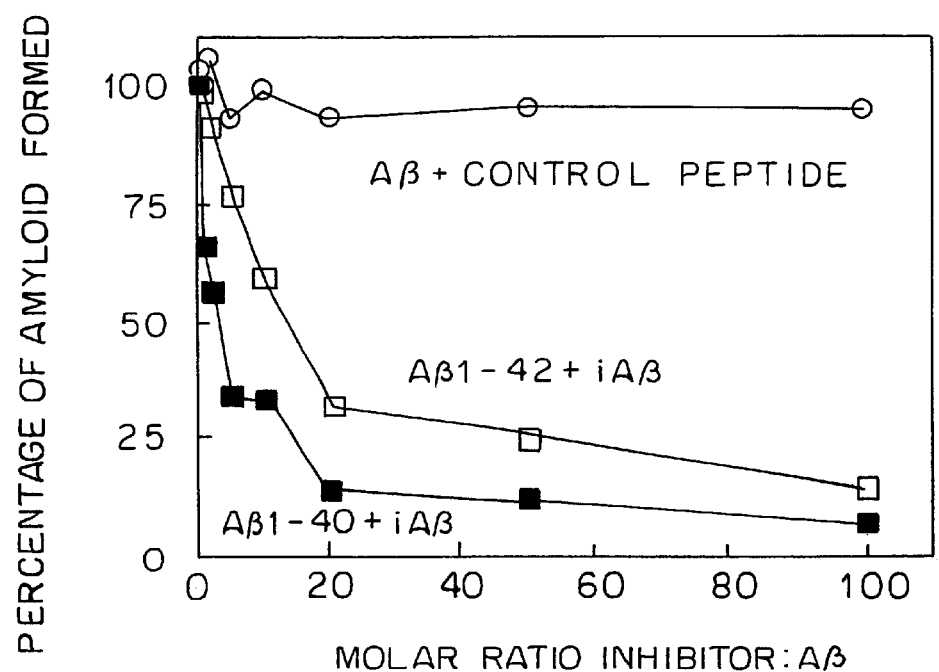
FIG. 12 shows the dose-dependent inhibition of Aβ1-40 and Aβ1-42 fibrillogenesis by iAβ. Amyloid formation was quantitated by the fluorometric assay, as described in Example 1. The β concentration was 1 mg/ml in 0.1 M Tris, pH 7.6 and an incubation time of 24 h.
Figure 13:
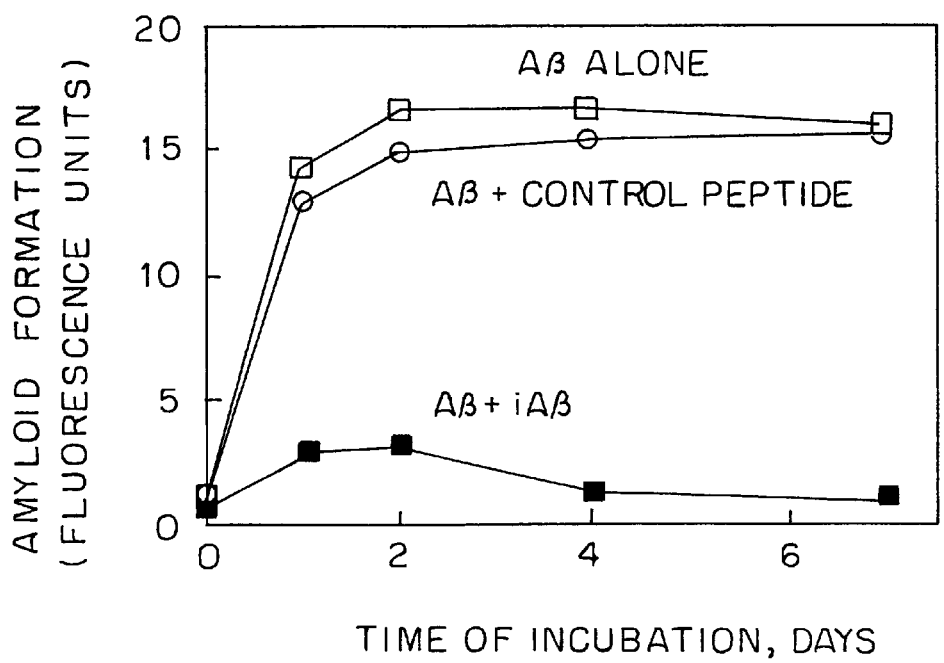
FIG. 13 shows the effect of iAβ on amyloid formation by Aβ1-40, after different incubation periods. The molar ratio Aβ:iAβ (or control) was 1:20; Aβ concentration 1 mg/ml. Amyloid formation was quantitated as in FIG. 12. iAβ or the control peptide alone did not give fluorescence values above the background level.

Inhibition of Aβ amyloid formation and dissolution of preformed fibrils in vitro The quantitative evaluation of the effect of iAβ on in vitro Aβ fibrillogenesis was based on a fluorometric assay that measures thioflavine T (Tht) fluorescence emission (Soto et al., 1995, supra). The binding of Tht to amyloid is specific and produces a shift in the emission spectrum of Tht and a fluorescent enhancement proportional to the amount of amyloid (LeVine et al., 1993, supra). FIG. 12 shows the influence of different concentrations of iAβ on fibrillogenesis of the two major variants of Aβ (Aβ1-40 and Aβ1-42). iAβ inhibited in a dose-dependent manner in vitro amyloid formation by both Aβ variants. After 24 h of incubation in the presence of a 5-fold or 20-fold molar excess of iAβ, Aβ1-40 formed only 33.9% and 13.7%, respectively, of the amyloid detectable in the absence of inhibitor (FIG. 12). Although the inhibitor is less efficient with Aβ1-42, a 5-, 20-, and 40-fold molar excess of iAβ over Aβ1-42 resulted in a 28.7%, 72.3% and 80.6% of inhibition, respectively (FIG. 12). Several non-related peptides had no effect on fibrillogenesis or slightly increased Aβ amyloid formation, probably by incorporation into the fibrils. The 12 residue control peptide (SEQ ID NO:26), did not alter amyloid formation by Aβ1-40 or Aβ1-42 (FIGS. 12 and 13). iAβ inhibited Aβ amyloid formation even after extensive incubation (FIG. 13) and appeared to be a more efficient blocker of fibrillogenesis after several days of incubation.

Figure 5A:
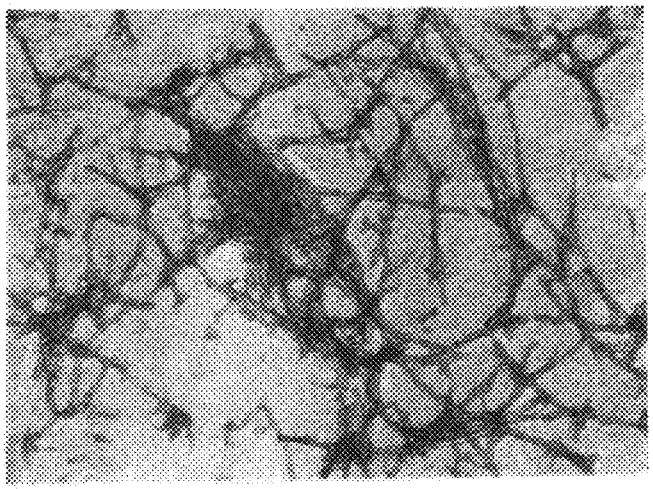
FIGS. 5A–C show electron micrographs of negative-stained preparations of Aβ (FIG. 5A), Aβ incubated with anti-amyloid peptide 1 (SEQ ID NO:7.
Figure 5B:
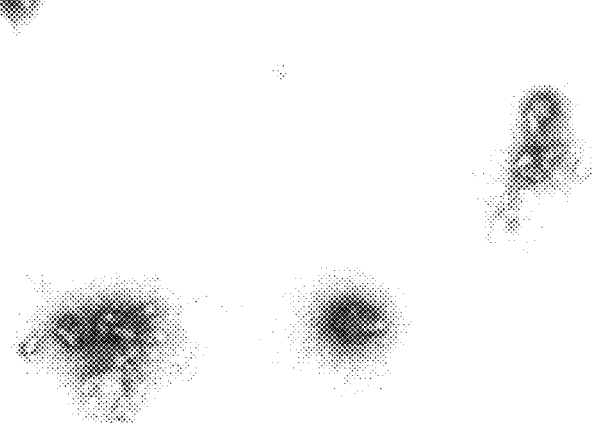
Figure 5C:
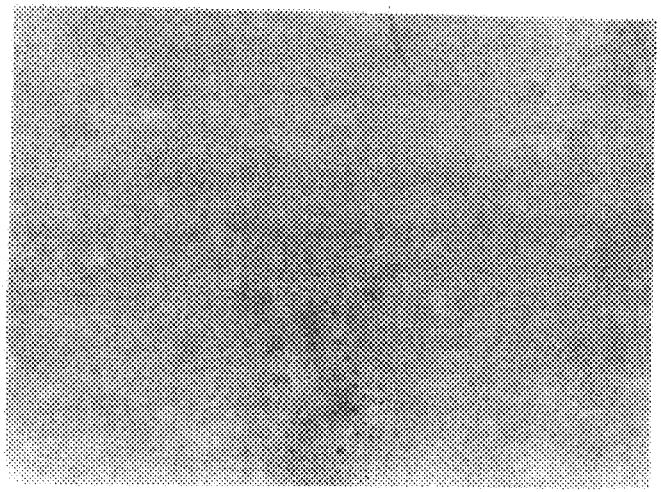

The 15-amino acid peptide, designated anti-amyloid peptide 1 (SEQ ID NO:7) was found to adopt a random coil conformation (FIG. 2B) and was also found to be 90% inhibitory to amyloid fibril formation at 50-fold molar excess over soluble amyloid monomers (FIGS. 5A and 5B).

Figure 14A:
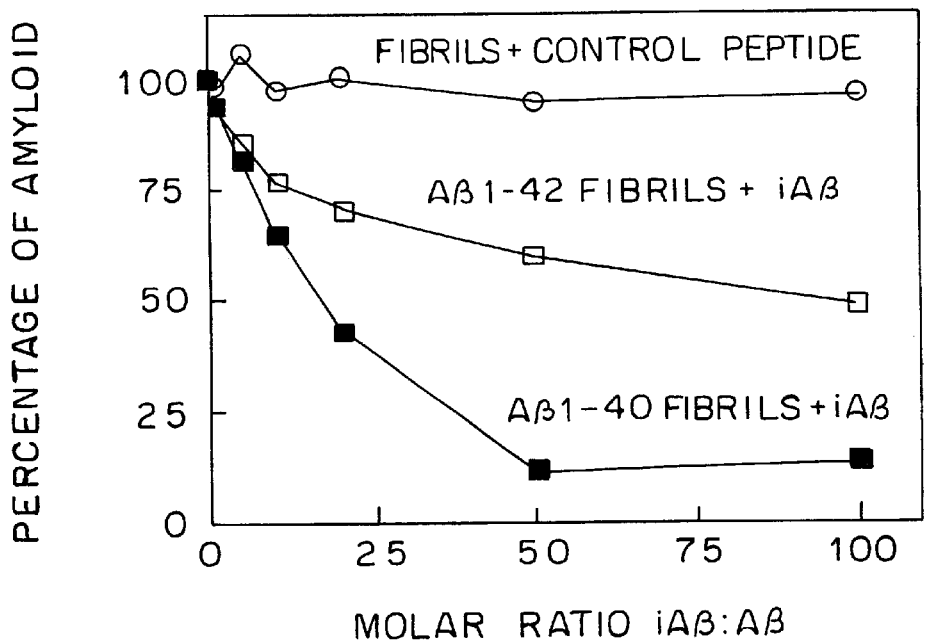
FIGS. 14A and 14B shows the dissolution of preformed Aβ fibrils by iAβ in vitro. Amyloid fibrils were first pre-formed by incubating Aβ1-40 or Aβ1-42 at a concentration of 1 mg/ml for 6 days at room temperature. Fluorometric quantitation of amyloid as described in Example 1.
Figure 14B:
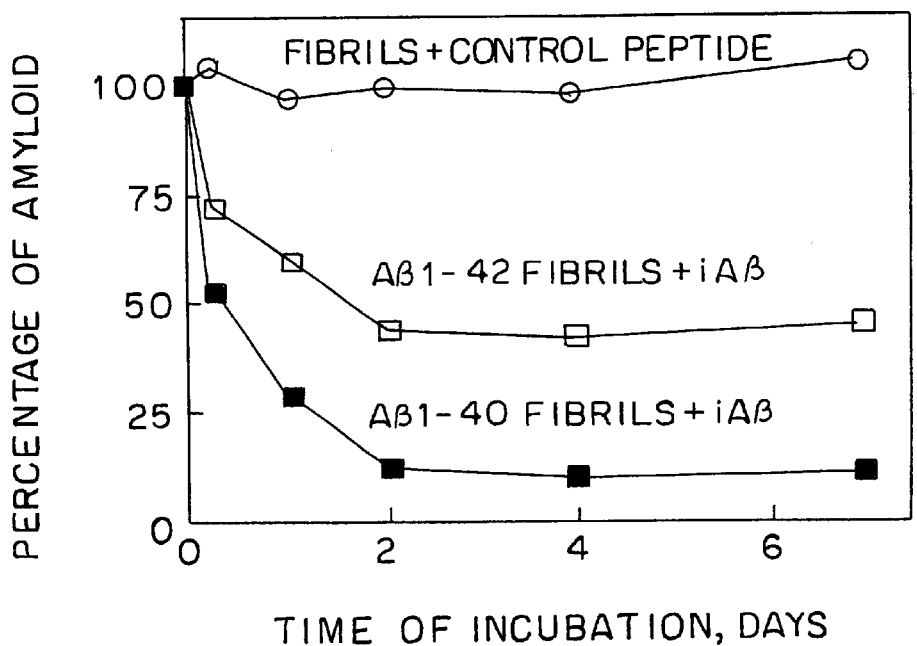

In order to evaluate the ability of iAβ to disassemble preformed Aβfibrils, Aβ1-40 or Aβ1-42 (1 mg/ml) were preincubated for 5 days at 37° C. before the addition of inhibitor peptide. FIG. 14A shows the dissolution of Aβ1-40 or Aβ1-42 fibrils after 24 h incubation with different iAβ concentrations. The inhibitor efficiently affected disaggregation of Aβ1-40 fibrils, achieving almost complete dissolution when used in a 40-fold molar excess. Conversely, only 51% of Aβ1-42 fibril reduction was obtained with the same molar excess of iAβ (FIG. 14). The maximum level of fibril dissolution was obtained after 2 days of incubation with iAβ and remained unaltered thereafter (FIG. 14B).

Figure 17:
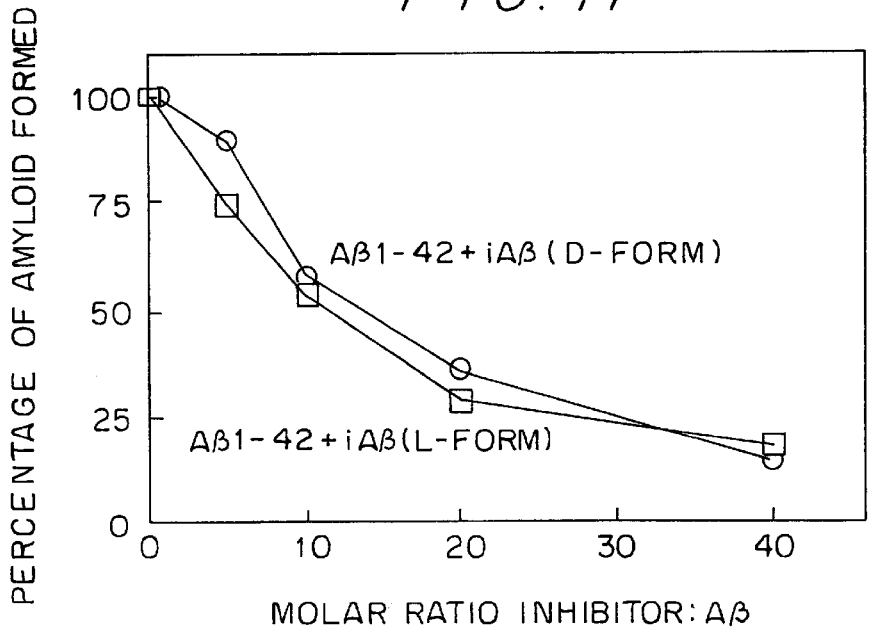
FIG. 17 shows the inhibition of Aβ fibrillogenesis by iAβ containing all D-amino acids.

The D-form of iAβ to inhibit Aβ fibrillogenesis was compared to the L-form of iAβ and the results shown in FIG. 17 demonstrate that D-iAβ inhibits Aβ fibrillogenesis similarly to L-iAβ. Aβ1-42 (1 mg/ml) was incubated for 24 h in the presence of different molar ratios of the L- and D-form of iAβ. Amyloid was quantitated by the fluorometric assay based on the thioflavine T fluorescence emission and expressed as a percentage of the amyloid obtained in the Aβ sample non-incubated with the inhibitor.

Figure 15A:
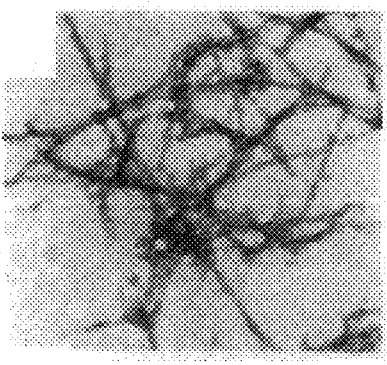
FIGS. 15a–f shows the electron microscopy analysis of the effect of iAβ on fibril formation and dissolution. Aliquots of Aβ1-40 (2 mg/ml) were incubated at 37° C. with or without iAβ or control peptide at a molar ratio 1:40 (Aβ:iAβ), centrifuged and the pellet loaded on electron microscopy grids, stained and visualized as described in the Materials and Methods.
Figure 15B:
Figure 15C:
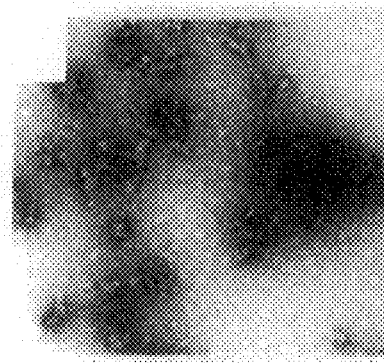
Figure 15D:
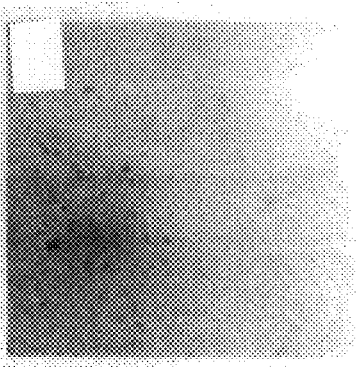
Figure 15E:
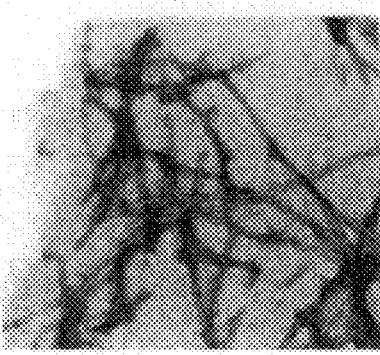
Figure 15F:
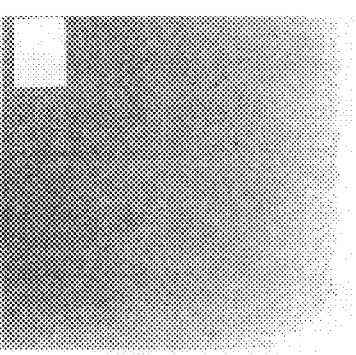
Figure 16:
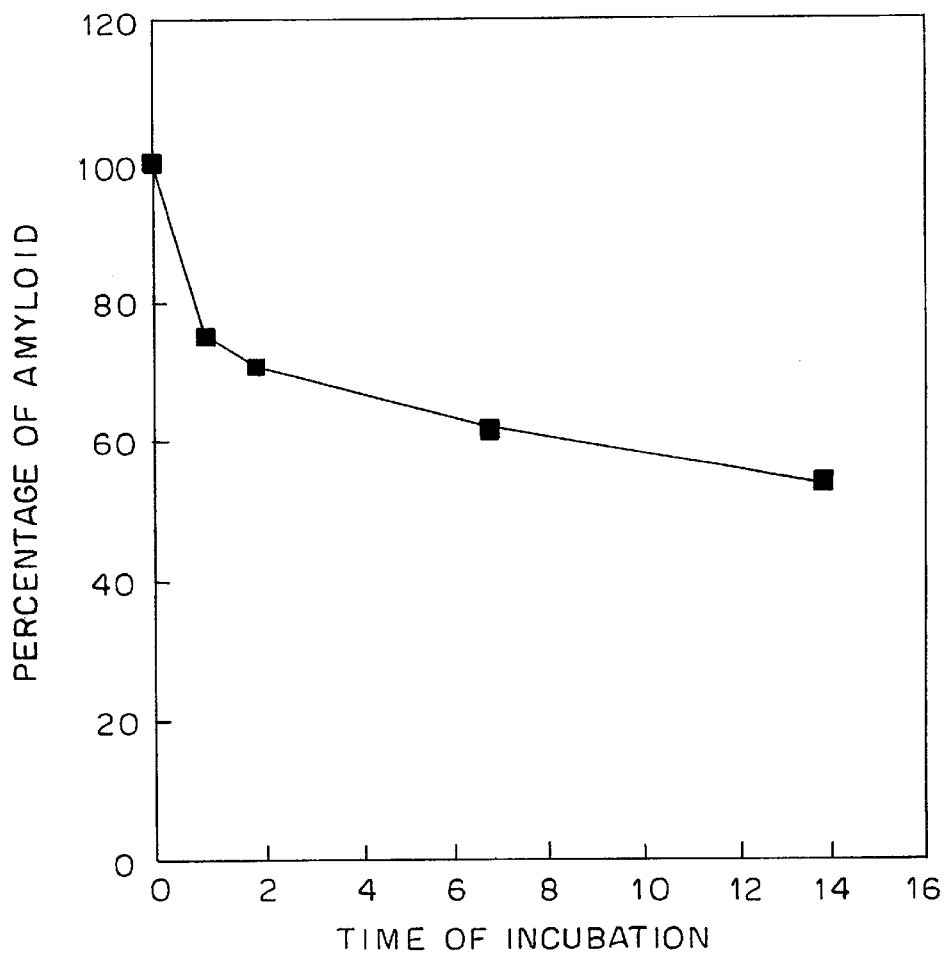
FIG. 16 shows the inhibition of amyloid formation after long period of incubation (days) in the presence of low concentrations of iAβ. 30 μg of Aβ1-42 was incubated in 30 μl of 0.1 M tris, pH 7.4 with a molar ratio 1:5 (Aβ:iAβ) of the inhibitor for different times at room temperature. Amyloid was quantitated by the thioflavine T fluorometric assay and expressed as a percentage of the amount of amyloid incubated for the same time in the absence of the inhibitor.

The inhibition of fibril formation and the dissolution of preformed fibrils by iAβ was also analyzed by negative-staining electron microscopy (FIGS. 15*a –f*). Aβ1-40 (2 mg/ml) preincubated for 6 days at 37° C. formed typical 8–10 nm unbranched fibrils (Castano et al., biochem. *Biophys. Res. Commun.* 141:782–789, 1986) (FIG. 15*a*). When Aβ was incubated from the start with a 40-fold excess of iAβ only amorphous aggregates were obtained (FIG. 15*b*). The control peptide under the same conditions did not produce any effect on Aβ fibrillogenesis (FIG. 15*e*). Fibrils preformed by incubation of Aβ1-40 for 6 days at 37° C. were almost completely dissolved after 2 days of incubation with a 1:40 molar ratio of Aβ:iAβ (FIG. 15*c*). iAβ or the control peptide incubated under the same conditions used in the experiments shown in FIGS. 15*b* and 15*e*, formed no amyloid-like material (FIGS. 15*d* and 15*f*).

Figure 6B:
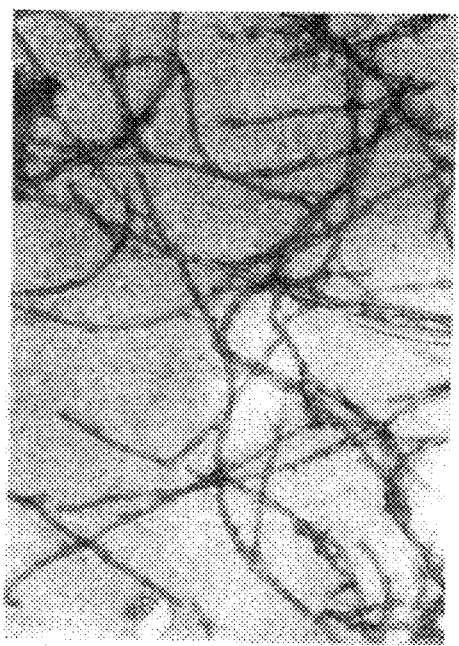
Figure 6B:
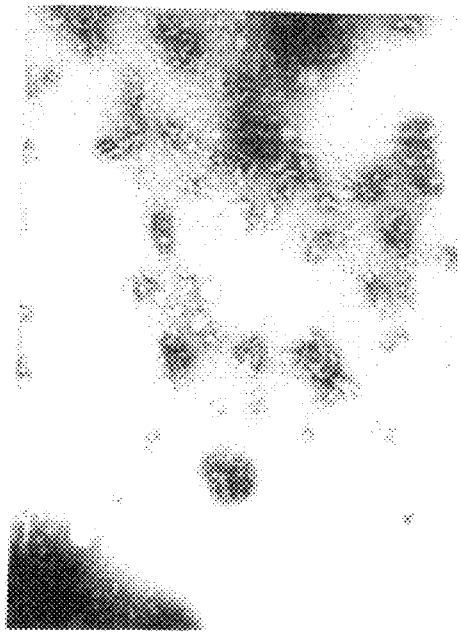
Figure 8:
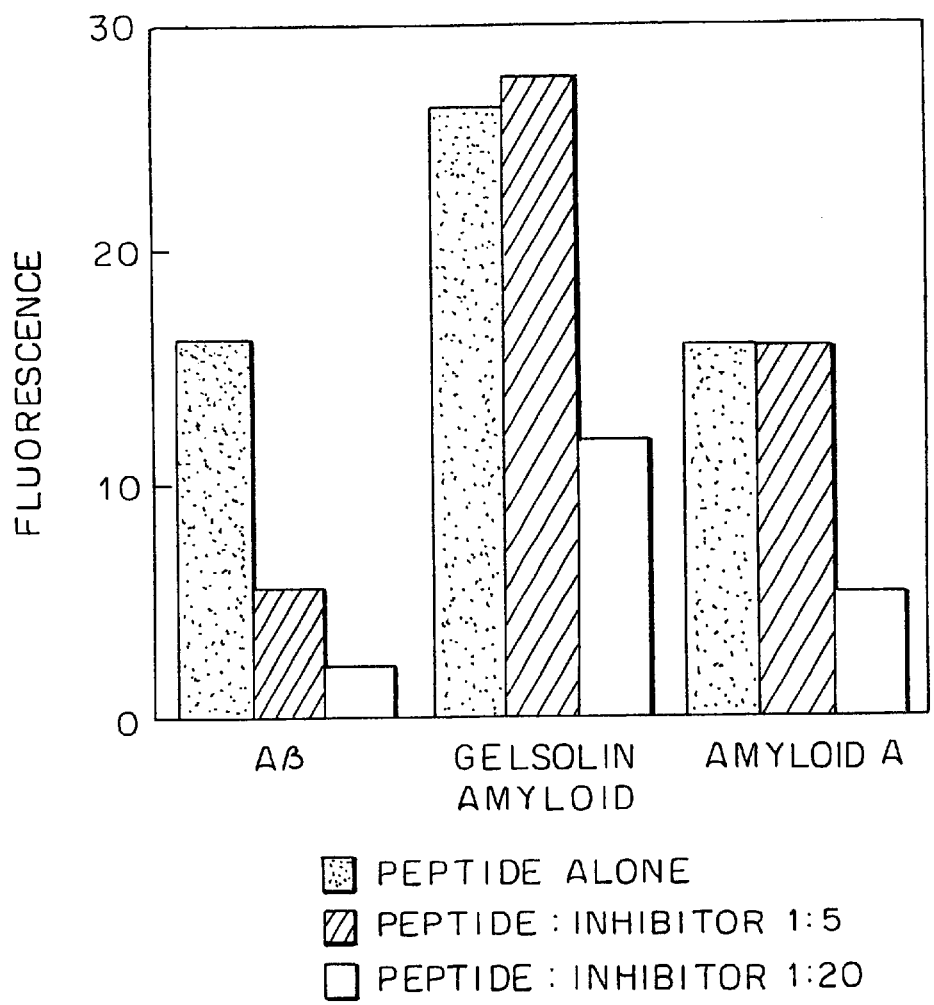
FIG. 8 is a bar graph showing the effect of anti-amyloid peptide 1 on the amyloid formation by Aβ and of peptides derived from the amyloidogenic sequence of gelsolin amyloid and amyloid A. Either β or the fifteen amino acid peptides containing the amyloidogenic sequence of gelsolin amyloid (SEQ ID NO: 12) and amyloid A (SEQ ID NO: 13) were incubated in a concentration of 1 mg/ml for 24 hours without and with anti-amyloid peptide 1 in a molar ratio of 1:5 or 1:20.

Dissolution of preformed fibrils also occurred with the 15 amino acid anti-amyloid peptide 1 (FIGS. 6A and 6B). This anti-amyloid peptide also inhibits the fibril formation of other amyloidgenic peptides derived from various other amyloid material, e.g., amyloid-A and the gelsolin related amyloid (FIG. 8).

Inhibition of in vivo fibrillogenesis using an animal model of amyloidosis related to amyloid-A. A well-characterized mouse model for systemic amyloid-A (AA) deposition was used. This model has been used to test the role of amyloid-associated components such as proteoglycans and apolipoprotein E (Kindy et al., Lab. Invest. 73:469–476, 1995; Snow et al., 1991, supra) and to test inhibitors of amyloid deposition in vivo (Kisilevsky et al., Nature Med. 1:143–148, 1995; Merlini et al., 1995, supra). Secondary or reactive amyloidosis is an inflammation-associated disorder in which AA protein is deposited in several organs. The AA protein is a 76 residues N-terminal fragment derived from proteolysis of a precursor called serum amyloid A (SAA) protein (Levin et al., 1972, supra).

Experimental amyloidosis in mice was induced by injection of amyloid enhancing factor (AEF) and silver nitrate. Under these conditions the animals developed amyloid deposits in the spleen after 36–48 h of the injection (Kisilevsky et al., 1983, supra). We examined the effect of iAβ on AA amyloid formation after 5 days. When 5 mg of iAβ were injected together with AEF, after 24 h of preincubation, the area occupied by amyloid in the spleen was decreased in approximately 86.4% in comparison with the animals treated without the inhibitor (Table 2).

TABLE 2

Effect of iAβ on in vivo amyloid deposition using the animal model of amyloid-A amyloidosis. Amyloid was induced by injection of amyloid enhancing factor (AEF) and silver nitrate (SN). Animals were sacrificed at 5 days and amyloid detected immunchistochemically using an antibody to serum amyloid A protein and quanitiated by image analysis, as described in Methods.

| Animal | AEF/SN | Control[a] untreated | AEF/SN + iAβ[b] |
|---|---|---|---|
| 1 | 29.4 | 0.05 | 4.35 |
| 2 | 31.65 | 0.1 | 3.68 |
| 3 | 32.97 | 0.21 | 5.32 |
| 4 | 30.77 | 0.04 | 3.67 |
| Average ± SE[c] | 31.2 ± 0.75 | 0.10 ± 0.04 | 4.26 ± 0.39 |

[a]Represents the grnup of animals not treated with AEF/SN
[b]AEF (100 μg) was preincubated with 5 mg of IBAP1 for 24 h and then injected together into the mice along with SN.
[c]Standard error Effect of iAβ on the promotion of Aβ fibrillogenesis induced by apoliprotein E. It is thought that sAβ in human body fluids is complexed to apolipoproteins, especially apolipoprotein (apo) J and E (Frangione et al., Neurobiol. Aging 15:97–99, 1994). These proteins as well as others (proteoglycans, amyloid P component, a1-antichymotrypsin, etc) are found in senile plaques and congophilic vessels (Coria et al., Lab. Invest. 58:454–457, 1988; Abraham et al., Cell 52:487–501, 1988; Wisniewski et al., Am. J. Pathol. 145:1030–1035, 1994; Snow et al., Neuron. 12:219–234, 1994). Several of these amyloid-associated proteins bind to Aβ in solution and modulate the rate of amyloid formation in vitro (Moore. G. J. Trends Pharmacol. Sci. 15:124–129, 1994; Wisniewski et al., Am. J. Pathol. 145:1030–1035, 1994; Ma et al., Nature 15i 372:92–94, 1994; Snow et al., Neuron. 12:219–234, 1994).

Figure 18:
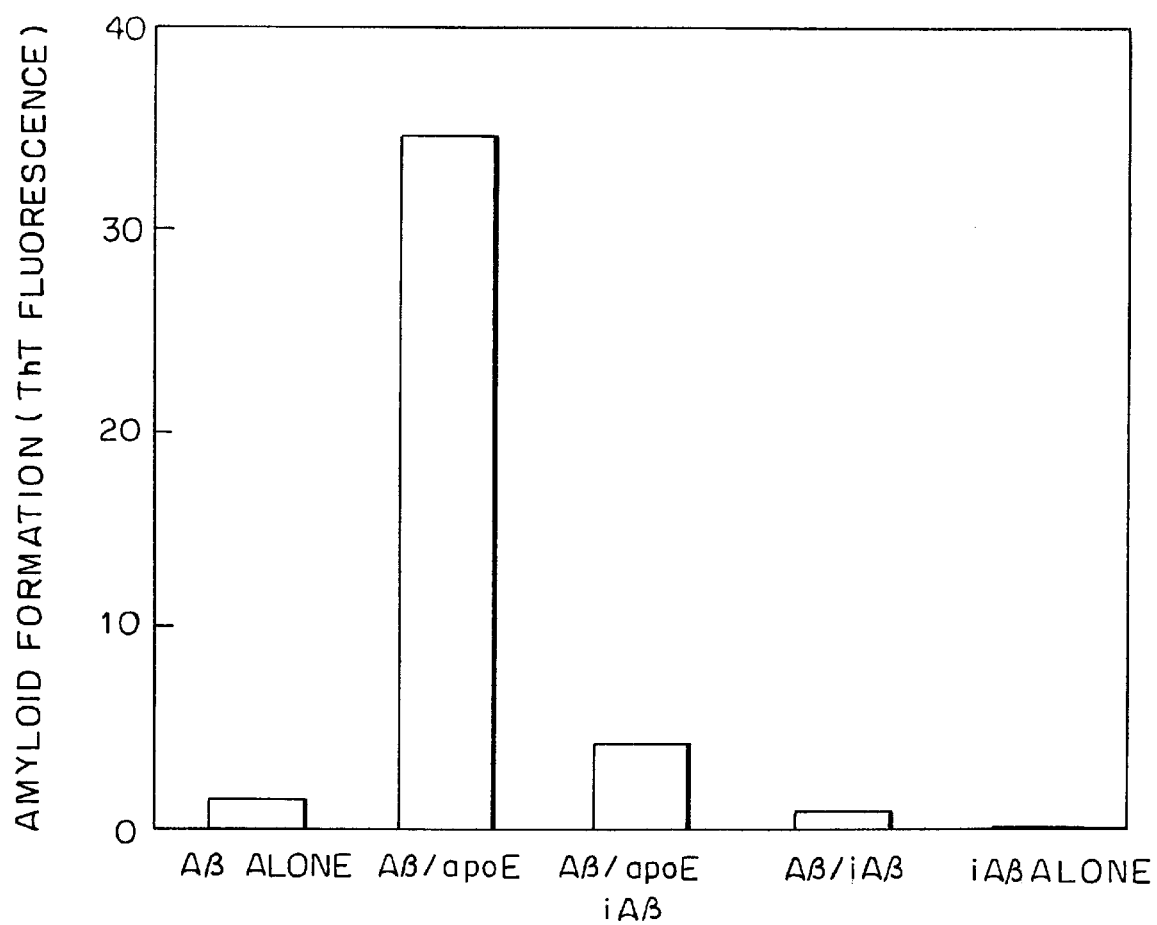
FIG. 18 shows the effect of iAβ on the promotion of β fibrillogenesis induced by apolipoprotein E. 30 μg of Aβ1-40 were incubated with or without 2.4 μg of human plasma apolipoprotein E (apoe). Samples of Aβ alone or Aβ/apoE were incubated also with 1:10 (Aβ:iAβ) of the inhibitor. All the incubations were performed for 24 h at room temperature. Amyloid formation was evaluated by the thioflavine T fluorometric assay. The average of two different experiments is shown.
Figure 19:
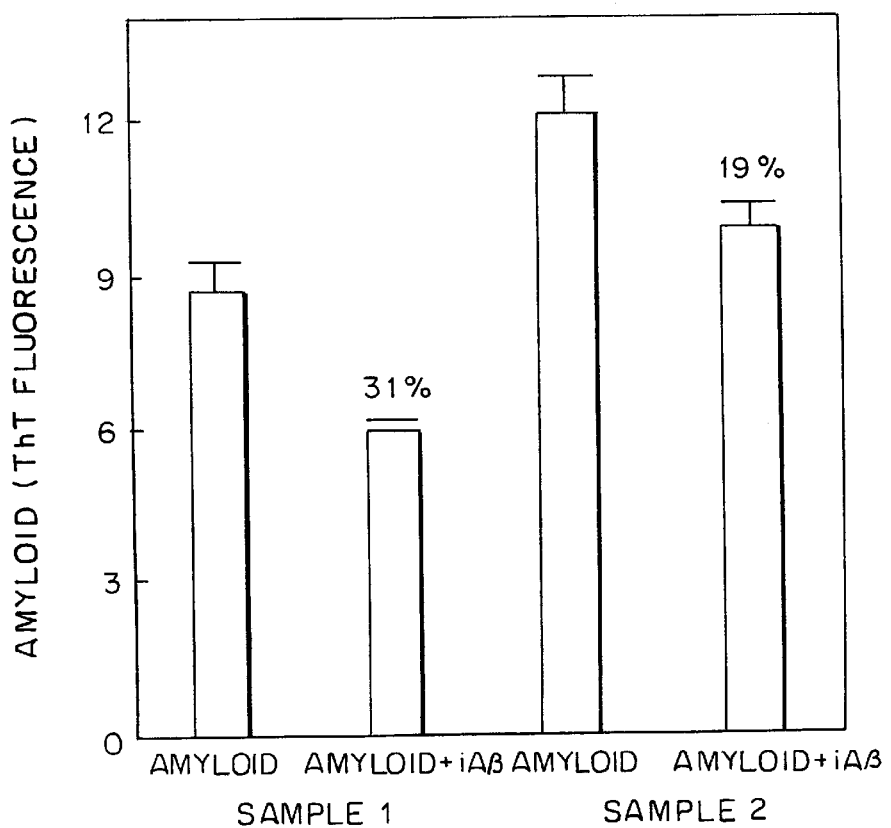
FIG. 19 shows Alzheimer's amyloid plaque dissolution by iAβ.
Figure 20:
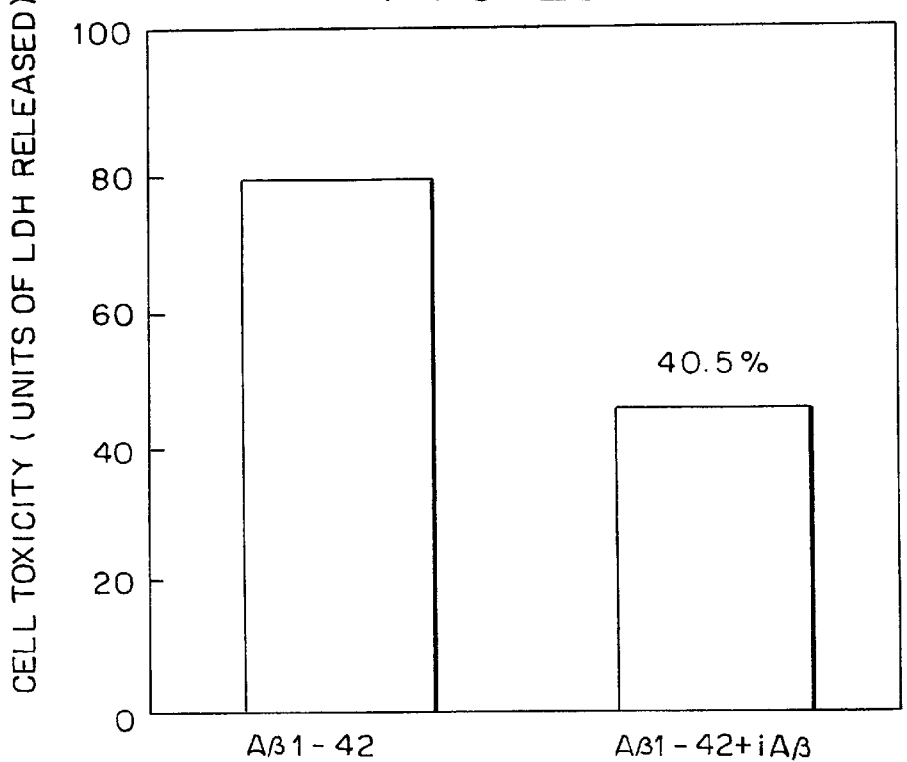
FIG. 20 shows the effect of iAβ on the Aβ-induced cell toxicity.

The results shown in FIG. 18 show that iAβ blocked the promotion of Aβ fibrillogenesis induced by apo E. Preliminary experiments also indicate that heparan-sulfate proteoglycan-induced Aβ fibrillogenesis is blocked as well by iAβ.

Dissolution of Alzheimer's amyloid plaque by iAβ. Amyloid was isolated from mature senile plaque extracted from a brain of a patient who died of Alzheimer's disease. Grey matter was separated from meninges and white matter, cleaned, chopped and homogenized in buffer containing 0.25M sucrose. The homogenate was subjected to a series of centrifugation, treatment with DNase I and collagenase and to a discontinuous sucrose density gradient. After this procedure, pure amyloid cores containing >90% Aβ and also several of the amyloid-associated proteins was obtained. 10 μg of amyloid proteins was incubated for 5 days without and with 200 μg of iAβ. The amount of amyloid was quantitated by using the fluorometric assay based in the binding of thioflavine T to amyloid, as described (Soto, C., et al., J. Biol. Chem. 270: 3063–3067, 1995). The material obtained from two different extractions was tested (Samples 1 and 2) and the average and standard error of three different experiments was shown.

Effect of iAβ on Aβ-induced cell toxicity. Neuronal differentiated human neuroblastoma cells (IMR-32) were obtained from American Type Culture Collection and were grown using the standard protocols. Fresh Aβ1-42 was added to the medium to reach a final concentration of 30 μM. The inhibitor (final concentration 600 μM) was added together or preincubated with Aβ1-42 for 24 h. After 48 h cell toxicity was evaluated by using the lactate dehydrogenase (LDH) release assay (Simmons, et al., Mol. Pharmacol. 45: 373–379, 1994), using a kit obtained from Sigma. The results shown correspond to the average between two different experiments.

Shorter iAβ derivatives. Shorter anti-β-sheet peptides were designed using peptide iAβ(SEQ ID NO:8) as a model (Table 3). Two frequent problems associated with peptides used as drugs in medicine, i.e., transport across the blood-brain barrier and generation of an immunoreactive response, can be minimized by shortening the length of the peptide. Studies on the inhibition of Aβ amyloid formation in vitro by iAβ derivatives showed that a seven (iAβ2) and a five (iAβ4) amino acid residue peptides are similar or better inhibitors than iAβ under the same experimental conditions (Table 3). In Table 3, 30 μg of Aβ peptides were incubated with a 10-fold molar excess of different peptides for 2 days at room temperature in 30 μl of 0.1M tris pH 7.6. The percentage of amyloid remaining after the incubation period was determined by the ThT fluorometric assay. Several control peptides (CP) and short Aβ fragments did not have any significatn efect on Aβ fibrillogenesis.

TABLE 3

Effect of iAβ derivatives on Aβ1-40 and Aβ1-42 amyloid formation

| Aβ incubated with | Sequence | % of amyloid Aβ1-42 | % of amyloid Aβ1-40 |
|---|---|---|---|
| alone | | 100 ± 1.7 | 100 ± 1.4 |
| iAβ | SEQ ID NO:8 | 57.9 ± 1.3 | 25.5 ± 0.7 |
| iAβ1 | SEQ ID NO:15 | 85.7 ± 11.6 | 55.2 ± 2.1 |
| iAβ2 | SEQ ID NO:16 | 61.3 ± 3.0 | 36.7 ± 4.8 |
| iAβ3 | SEQ ID NO:17 | 87.1 ± 6.1 | 90.1 ± 1.3 |
| iAβ4 | SEQ ID NO:18 | 45.4 ± 0.6 | 28.7 ± 1.7 |
| iAβ5 | SEQ ID NO:19 | 82.4 ± 5.0 | 92.1 ± 1.3 |
| iAβ6 | Pro-Phe-Phe | 88.9 ± 2.6 | 108.1 ± 7.9 |
| CP1 | SEQ ID NO:49 | 101.3 ± 1.9 | 98.4 ± 1.2 |
| CP2 | SEQ ID NO:66 | 125.3 ± 3.9 | 111.3 ± 4.1 |
| CP3 | SEQ ID NO:67 | 94.4 ± 1.4 | 87.7 ± 2.0 |

TABLE 3-continued

Effect of iAβ derivatives on Aβ1-40 and Aβ1-42 amyloid formation

| Aβ incubated with | Sequence | % of amyloid Aβ1-42 | % of amyloid Aβ1-40 |
|---|---|---|---|
| Aβ10-20 | SEQ ID NO:68 | 80.9 ± 1.6 | 73.1 ± 0.9 |
| Aβ17-21 | a.a. 2-6 of SEQ ID NO:1 | 92.3 ± 3.4 | 89.2 ± 2.7 |
| Aβ18-21 | a.a. 3-6 of SEQ ID NO:1 | 98.5 ± 5.3 | 105 ± 3.2 |

EXAMPLE 2

Cerebral deposition of PrP amyloid occurs in most of the cases of the PrP-related disorder known as Gerstmann-Straussler-Scheinker (GSS) disease. The major component of 5 amyloid fibrils in GSS brains is a 11-kDa fragment of PrP that spans residues 58 to 150 (Tagliavini, F., et al. *EMBO J.* 10:513–519, 1991). By using the synthetic peptides homologous to the consecutive segments of GSS-amyloid protein, it has been shown that the PrP fragment 109–141 is critical in conferring the pathological properties of PrP$^{sc}$ (Nguyen, J., et al. *Biochem.* 34:4186–4192, 1995; Zhang, H., et al., *J. Mol. Biol.* 250:514–526, 1995; Tagliavini, F. et al. *Proc. Natl. Acad. Sci. (USA)* 90:9678–9682, 1993). The peptide 109–141 (SEQ ID NO:37) as well as the peptide fragments 109–122 (SEQ ID NO:34) and 106–126 (SEQ ID NO:35), but not peptide fragment 129–141 (SEQ ID NO:36), formed typical amyloid fibrils (Zhang H. et al. *J. Mol. Biol.* 250:514–526, 1995; Gassett, Baldwin, Lloyd, et al. 1992; Tagliavini, F., et al. *Proc. Natl. Acad. Sci. (USA)* 90:9678–9862, 1993). In addition, the PrP fragment 109–122, (which adopts a β-sheet conformation) can convert the unstructured fragment 129–141 into a β-pleated sheet (Nguyen, J., et al. *Biochem.* 34:4186–4192, 1995). Moreover, the fragments 90–145 and 109–141 are resistant to degradation by proteinase K when they adopt a β-sheet conformation (Zhang, H., et al. *J. Mol. Biol.* 250:514–526, 1995). Finally, the peptide fragment 90–145, which adopts a β-sheet conformation, can induce the conversion of PrP$^c$ into PrP$^{sc}$ in vitro (Kaneko, K. et al., *Proc. Natl. Acad. Sci. USA* 92:11160–11165, 1995).

Figure 21:
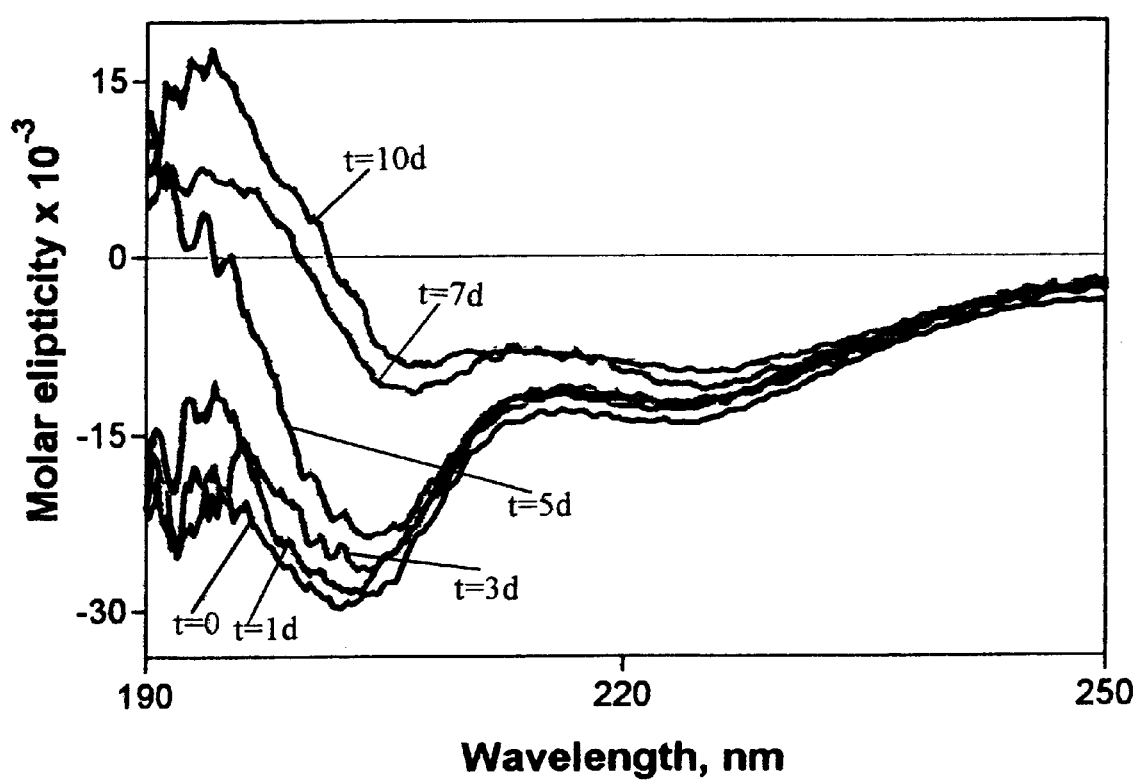
FIG. 21 shows the change in the conformation of the PrP 109-141 fragment as evaluated by circular dichroism at time points of 0, 1, 3, 5, 7 and 10 days.

The experiments described below were carried out using a synthetic peptide corresponding to the 109–141 fragment of PrP as a model system for the conformational transition that is observed in the formation of the pathogenic PrP$^{sc}$ isoform. This synthetic peptide corresponding to the sequence 109–141 of PrP, designated PrP 109–141, undergoes spontaneous conversion from an initial random coil to adopt a β-sheet secondary structure in a period of a few days, as evaluated by circular dichroism (FIG. 21), using the conditions described in Nguyen, J. et al. *Biochem.* 34:4186–4192 (1995). Briefly, aliquots of 80 μg of PrP109–141 were incubated for 0, 1, 3, 5, 7 and 10 days at 37° C. in 350 μl of 0.1M sodium phosphate, pH 5, 50% acetonitrile. The circular dichroism spectra was measured as described in Soto and Castano, *Biochem. J.* 314:701–707, 1996. A negative peak at approximately 200 nm is indicative of a random coil structure, while a positive peak at 195 nm and a negative peak at 220 nm is typical of β-sheet structures (Greenfield, N. & Fasman, G. D. *Biochem.* 8:4108–4116, 1969). FIG. 21 shows that PrP109–141 converts from a random coil conformation to a β-sheet structure over time.

Figure 22:
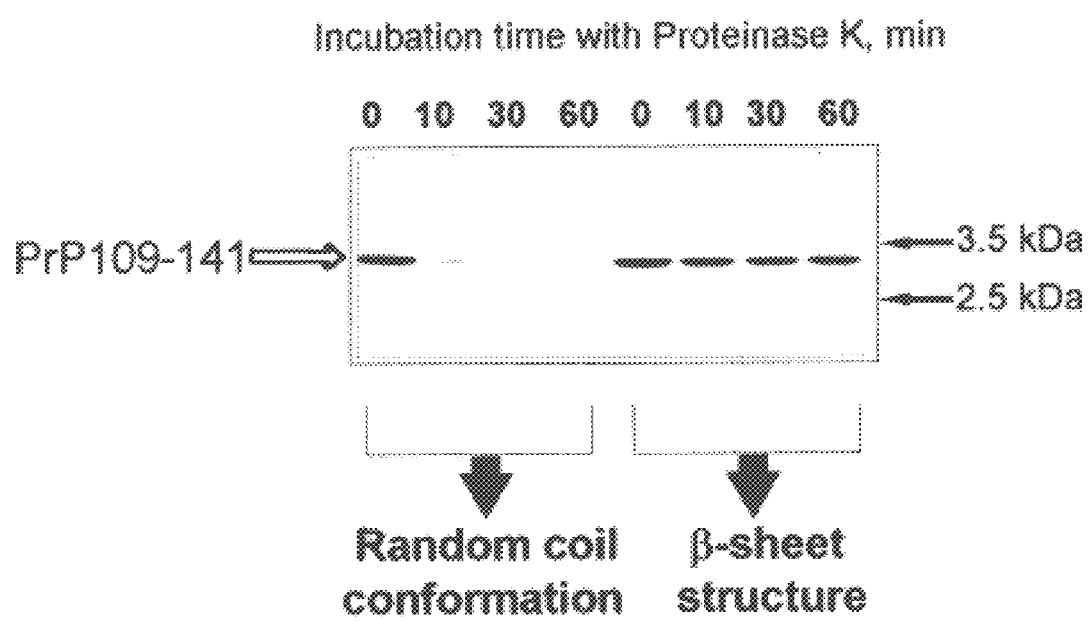
FIG. 22 shows samples of the PrP 109-141 fragment in a random coil or β-sheet conformation being treated with proteinase K and electrophoresed on SDS polyacrylamide gel. Arrows on the left indicate the position of molecular weight standards.

In addition, when the PrP109-141 peptide adopts a β-sheet conformation, it is highly resistant to degradation by proteinase K (FIG. 22), whereas the same peptide in a random coil structure is highly degradable by this protease. This is shown in FIG. 22 where aliquots of PrP109-141 were incubated as indicated above for the circular dichroism study for 7 days to obtain a peptide adopting a β-sheet conformation. The sample was then lyophilized and resuspended in Phosphate buffered saline (PBS). A similar aliquot of the fragment, without pre-incubation (adopting a random coil conformation), was also resuspended in PBS. Both samples were treated with proteinase K (1:400 w/w) for 0, 10, 30 and 60 min. The reaction was stopped by adding 5 mM phenylmethyl-sulphonylfluoride (PMSF) and sample buffer for electrophoresis. Samples having the equivalent of 5 μg of PrP109-141 per lane were separated by SDS electrophoresis in Tris-Tricine buffer (Schagger, H. & vonjagow, G., *Anal. Biochem.* 166:368–379, 1987) and stained with Coomasie blue. The result that PrP109-141 in the β-sheet conformation is resistant to proteinase K degradation is very similar to the differences in proteinase K sensitivity observed between PrP$^{sc}$ and PrP$^c$.

Moreover, the PrP109-141 fragment as well as the PrP fragment 106-126 form typical amyloid fibrils when incubated for several days under physiological conditions, as evaluated by electron microscopy (FIG. 23A). FIGS. 23A and 23B show the electron microscopy pattern obtained when PrP109-141 was incubated alone (FIG. 23A) or in the presence of 10-fold molar excess of iPrP-12aa (FIG. 23B), a prototype PrP peptide inhibitor (12 amino acid residues; SEQ ID NO:24) that was first screened for its ability to inhibit amyloid formation by PrP fragments in vitro. Aliquots of PrP109-141 (2 mg/ml) were incubated for 7 days at 37° C. without (FIG. 23A) or with (FIG. 23B) 10-fold molar excess of iPrP-12aa. The samples were first centrifuged at 14,000 rpm for 5 min and the pellet was resuspended in half of the initial volume and placed on carbon formar-coated 300-mesh nickel grids. The grids were stained for 60 seconds with 2% uranyl acetate under a vapor of 2% glutaraldehyde and visualized on a Zeiss EM 10 electron microscope at 80 kV. A reduction in the number of fibrils was clearly observed when the PrP fragment was incubated with the inhibitor.

Figure 24:
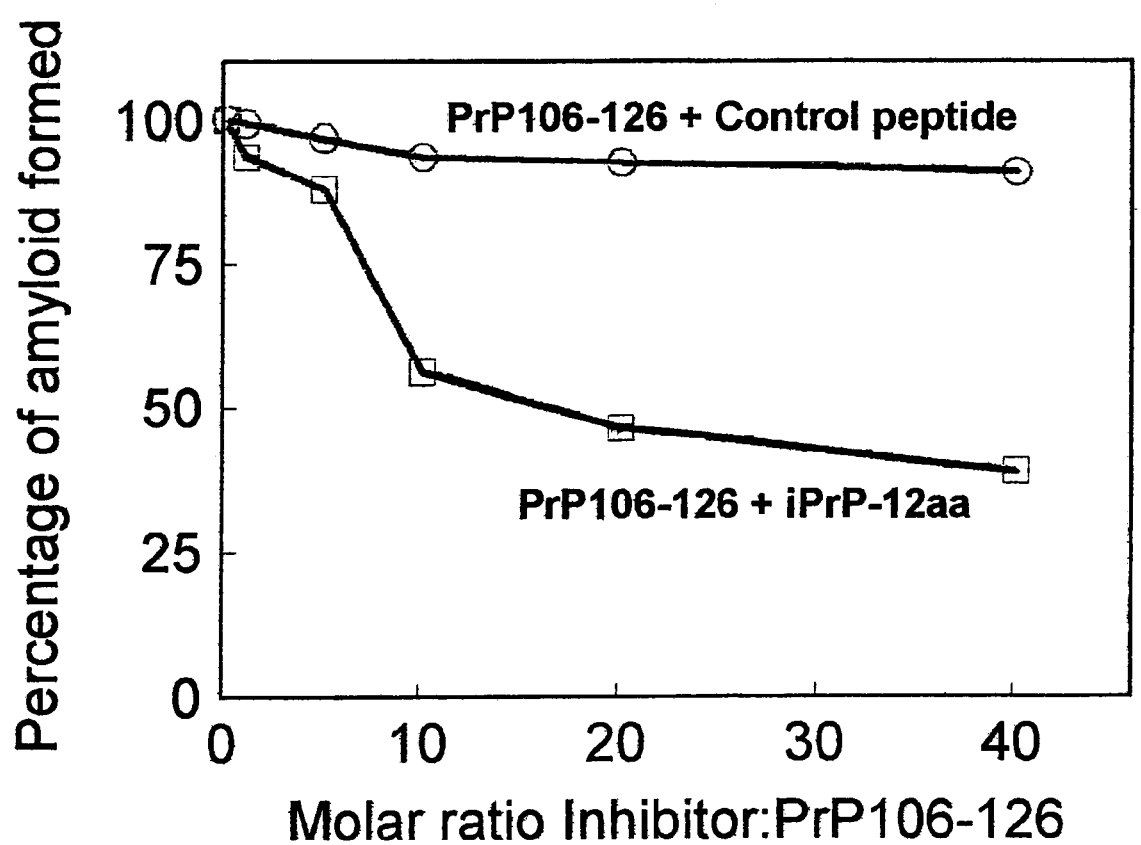
FIG. 24 shows the dose-dependent inhibition of PrP106-126 peptide fibrillogenesis by iPrP-12aa. The control peptide is CP1 (SEQ ID NO:49).
Figure 25:
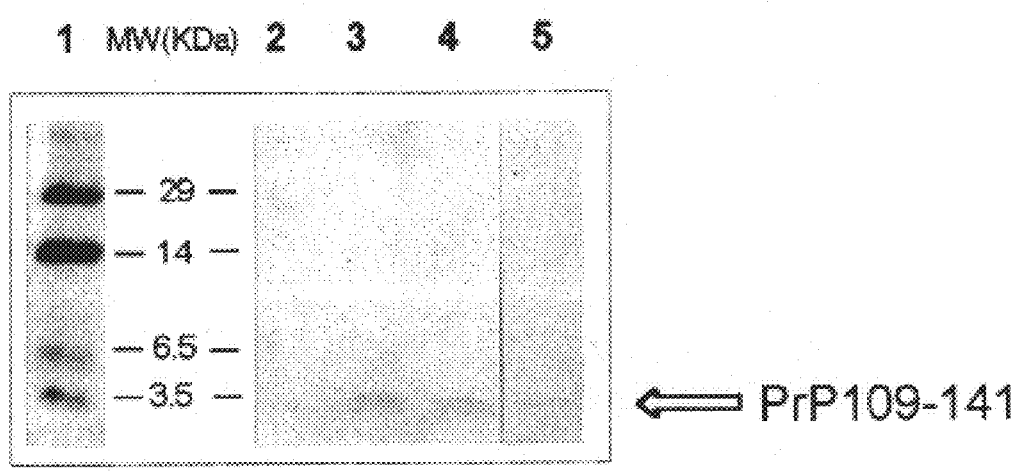
FIG. 25 shows the influence of iPrP-12aa on proteinase K degradation of PrP109-141 as determined by SDS-PAGE. Aliquots of PrP109-141 were converted from random coil to β-sheet by incubation for 7 days under the conditions described in Example 2 for the circular dichroism study in the absence (lane 3) or in the presence of 10-fold molar excess of an unrelated control peptide (CP1) (lane 4) or iPrP-12aa (lane 5). The sample was then lyophilized and resuspended in PBS. A similar aliquot of the fragment that was not pre-incubated (adopting a random coil conformation) was also lyophilized and resuspended in PBS (lane 2). The samples were treated with proteinase K (1:400 w/w) for 60 min. The reactions were then stopped and the samples analyzed by electrophoresis as described above for the results shown in FIG. 22. Lane 1 corresponds to molecular weight standards.
Figure 26:
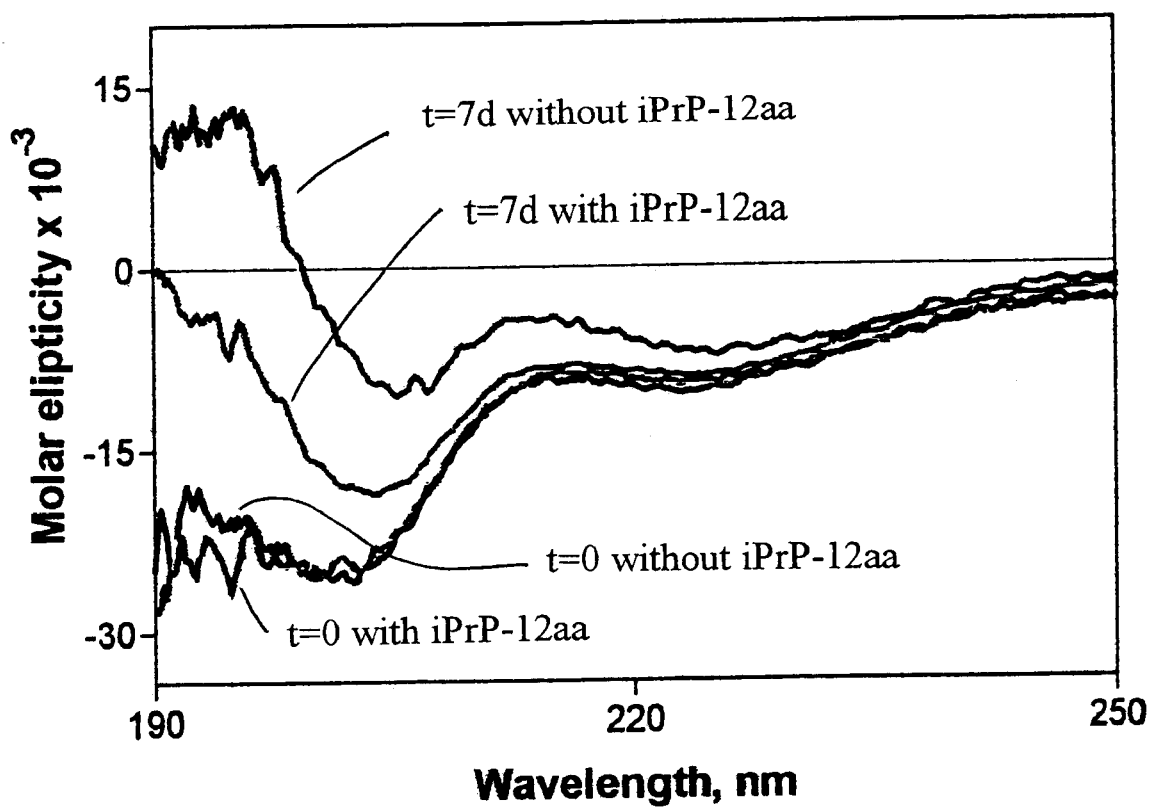
FIG. 26 shows the inhibition of PrP109-141 conformational transition with inhibitor peptide iPrP-12aa as evaluated by circular dichroism at t=0 and t=7 days.

FIG. 24 shows the dose-dependent inhibition of PrP106-126 fibrillogenesis by iPrP-12aa. Amyloid formation was quantitated by the fluorometric assay, based on the specific interaction of Thioflavine T (Tht) with amyloid fibrils. PrP106-126 at 1 μg/μl in PBS, pH 7.4, was incubated for 5 days at 37° C., and at the end of the incubation period, 50 mM glycine, pH 9.2, 2 μM Tht was added in a final volume of 2 ml. Fluorescence was measured at an excitation wavelenth of 435 nm and an emission wavelength of 485 nm in a Perkin Elmer, model LS50B fluorescence spectrometer. Approximately, 50% inhibition of amyloid formation was observed in the presence of a 10-fold molar excess of iPrP-12aa. No significant effect was seen when the PrP fragment was incubated with the same concentration of an unrelated peptide of 12 amino acids (CPI; SEQ ID NO:49). Peptide iPrP-12aa was also able to partially block the conversion of PrP109-141 from a protease-sensitive (random coil conformation) (FIG. 25). In fact, while almost 100% of the PrP peptide molecules after incubation for 5 days in the absence of the inhibitor were resistant to proteinase K, less than 50% of the PrP peptide molecules were resistant when the PrP fragment was incubated in the presence of a 10-fold molar excess of iPrP-12aa (FIG. 25). Since the differences in protease degradability are associated with the secondary structure adopted by the peptide (FIG. 22), the latter result demonstrates that peptide iPrP-12aa is able to function as a peptide inhibitor and block the conversion of random coil→β-sheet in the peptide model of PrP. This conclusion is supported by direct evaluation of the effect of iPrP-12aa on the conformational transition of PrP109-141 (FIG. 26). When 80 μg aliquots of the 109-141 fragment were incubated alone for 7 days as described previously in this example for circular dichroism studies, the spontaneous transformation of an initial random coil structure to a β-sheet rich conformation was observed. However, when PrP109-141 was incubated under the same conditions, but in the presence of 10 μg of iPrP-12aa (molar ratio peptide inhibitor=2.5:1), the extent of conformational change was clearly lower (FIG. 26). In short, these results indicate that anti-β sheet peptides designed to interact with PrP109-141 in view of the PrP sequence can be used to prevent the in vitro transformation of $PrP^c \rightarrow PrP^{sc}$, as determined by using the peptide model system described above.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. An isolated inhibitory peptide consisting of an amino acid sequence selected from the group consisting of SEQ ID NO:7, 8, 9, 10, 15, 16, 17, 18, 19, 20, 21, 22, 24, 25, 27, 28, 29, 30, 31, 32, 33, 38, 39, 40, 41, 42, 43, 44, 45, 46, 47, 48 and Pro-Pro-Phe.

2. The isolated inhibitory peptide in accordance with claim 1, wherein at least some amino acid residues of said sequence are amino acid derivatives.

3. The isolated inhibitory peptide in accordance with claim 1, wherein the inhibitory peptide has the amino acid sequence of SEQ ID NO:40.

4. The isolated inhibitory peptide in accordance with claim 1, wherein at least some amino acid residues of said sequence are D-amino acid residues.

5. A composition, comprising the isolated inhibitory peptide of claim 1 and a pharmaceutically acceptable carrier.

6. An isolated inhibitory peptide, consisting of an amino acid sequence selected from the group consisting of SEQ ID NO:8, 15, 16, 17, 18, and 19.

7. The isolated inhibitory peptide in accordance with claim 6, wherein the peptide consists of the amino acid sequence of SEQ ID NO:8.

8. The isolated inhibitory peptide in accordance with claim 6, wherein the peptide consists of the amino acid sequence of SEQ ID NO:18.

9. The isolated inhibitory peptide in accordance with claim 6, wherein at least some amino acid residues of said sequence are D-amino acid residues.

10. The isolated inhibitory peptide in accordance with claim 6, wherein at least some amino acid residues of said sequence are amino acid derivatives.

11. A composition, comprising the isolated inhibitory peptide of claim 6 and a pharmaceutically acceptable carrier.

12. The composition of claim 11, wherein the isolated inhibitory peptide comprises the amino acid sequence of SEQ ID NO:8.

13. An isolated inhibitory peptide, consisting of an amino acid sequence selected from the group consisting of SEQ ID NO:24 and 40.

14. The isolated inhibitory peptide in accordance with claim 13, wherein at least some amino acid residues of said sequence are D-amino acid residues.

15. A composition, comprising the isolated inhibitory peptide of claim 13 and a pharmaceutically acceptable carrier.

16. The isolated inhibitory peptide in accordance with claim 13, wherein at least some amino acid residues of said sequence are amino acid derivatives.

* * * * *

```
                          SEQUENCE LISTING (1) GENERAL INFORMATION:

(iii) NUMBER OF SEQUENCES: 69

(2) INFORMATION FOR SEQ ID NO:1:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:1:

Lys Leu Val Phe Phe Ala Glu Asp
1               5

(2) INFORMATION FOR SEQ ID NO:2:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:2:

Arg Ser Phe Phe Ser Phe Leu Gly
1               5
```

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Asp Cys Phe Ile Leu Asp Leu Gly
1          5

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Arg Val Thr Ile Thr Cys Gln Ala
1          5

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ser Phe Tyr Leu Leu Tyr Tyr Thr
1          5

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Asp Leu Ala Thr Val Tyr Val Asp
1          5

(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Ser Arg Gly Asp Leu Pro Phe Phe Pro Val Pro Ile Gly Asp Ser
1          5                10              15

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Arg Asp Leu Pro Phe Phe Pro Val Pro Ile Asp
1               5                   10
```

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Arg Asp Phe Ile Pro Leu Pro Leu Asp
1               5
```

(2) INFORMATION FOR SEQ ID NO:10:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Arg Asp Tyr Leu Pro Tyr Tyr Pro Leu Asp
1               5                   10
```

(2) INFORMATION FOR SEQ ID NO:11:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Gly Lys Met Ser Ser Tyr Ala Phe Phe Val Gln Thr Cys Arg Glu Glu
1               5                   10                  15
His Lys
```

(2) INFORMATION FOR SEQ ID NO:12:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Phe Asn Asn Gly Asp Cys Phe Ile Leu Asp Leu Gly Asn Asn Ile
1               5                   10                  15

(2) INFORMATION FOR SEQ ID NO:13:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Arg Ser Phe Phe Ser Phe Leu Gly Glu Ala Phe Asp Gly Ala Arg
1               5                   10                  15

(2) INFORMATION FOR SEQ ID NO:14:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Gln Lys Leu Val Phe Phe Ala Glu Asp Val Gly
1               5                   10

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Arg Asp Leu Pro Phe Phe Pro Val Asp
1               5

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Leu Pro Phe Phe Pro Val Asp
1               5

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Leu Pro Phe Phe Val Asp
1               5

(2) INFORMATION FOR SEQ ID NO:18:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Leu Pro Phe Phe Asp
1               5

(2) INFORMATION FOR SEQ ID NO:19:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Leu Pro Phe Phe
1

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Arg Asp Leu Pro Ile Val Pro Leu Pro Ile Asp
1               5                   10

(2) INFORMATION FOR SEQ ID NO:21:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Leu Pro Ile Val Pro Leu Asp
1               5

(2) INFORMATION FOR SEQ ID NO:22:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Leu Pro Ile Val Asp
1               5

(2) INFORMATION FOR SEQ ID NO:23:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Gly Ala Ala Ala Ala Gly Ala Val Val Gly Gly Leu
1               5                   10

(2) INFORMATION FOR SEQ ID NO:24:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Arg Asp Ala Pro Ala Ala Pro Val Val Pro Leu Asp
1               5                   10

(2) INFORMATION FOR SEQ ID NO:25:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Ala Ala Pro Val Val Pro Asp
1               5

(2) INFORMATION FOR SEQ ID NO:26:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Val His Val Ser Glu Glu Gly Thr Glu Pro Glu Ala
1               5                   10

(2) INFORMATION FOR SEQ ID NO:27:

(i) SEQUENCE CHARACTERISTICS:
        (A) LENGTH: 5 amino acids
        (B) TYPE: amino acid
        (C) STRANDEDNESS: single
        (D) TOPOLOGY: linear

```
      (ii) MOLECULE TYPE: peptide (xi) SEQUENCE DESCRIPTION: SEQ ID NO:27:

Leu Val Pro Phe Asp
1               5

(2) INFORMATION FOR SEQ ID NO:28:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:28:

Leu Phe Pro Phe Asp
1               5

(2) INFORMATION FOR SEQ ID NO:29:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:29:

Pro Leu Phe Phe Asp
1               5

(2) INFORMATION FOR SEQ ID NO:30:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:30:

Leu Val Phe Pro Asp
1               5

(2) INFORMATION FOR SEQ ID NO:31:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:31:

Lys Leu Pro Phe Phe
1               5

(2) INFORMATION FOR SEQ ID NO:32:

(i) SEQUENCE CHARACTERISTICS:
           (A) LENGTH: 5 amino acids
           (B) TYPE: amino acid
           (C) STRANDEDNESS: single
           (D) TOPOLOGY: linear
```

```
        (ii) MOLECULE TYPE: peptide (xi) SEQUENCE DESCRIPTION: SEQ ID NO:32:

Lys Leu Val Pro Phe
1               5

(2) INFORMATION FOR SEQ ID NO:33:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:33:

Lys Pro Val Phe Phe
1               5

(2) INFORMATION FOR SEQ ID NO:34:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:34:

Met Lys His Met Ala Gly Ala Ala Ala Ala Gly Ala Val Val
1               5                   10

(2) INFORMATION FOR SEQ ID NO:35:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:35:

Lys Thr Asn Met Lys His Met Ala Gly Ala Ala Ala Ala Gly Ala Val
1               5                   10                  15
Val Gly Gly Leu Gly
            20

(2) INFORMATION FOR SEQ ID NO:36:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:36:

Met Leu Gly Ser Ala Met Ser Arg Pro Met Met His Phe
1               5                   10

(2) INFORMATION FOR SEQ ID NO:37:

(i) SEQUENCE CHARACTERISTICS:
```

(A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Met Lys His Met Ala Gly Ala Ala Ala Gly Ala Val Val Gly Gly
1               5                  10                  15

Leu Gly Gly Tyr Met Leu Gly Ser Ala Met Ser Arg Pro Met Met His
            20                  25                  30

Phe (2) INFORMATION FOR SEQ ID NO:38:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Arg Asp Ala Pro Ala Ala Pro Ala Gly Pro Val Val Pro Leu Asp
1               5                  10                  15

(2) INFORMATION FOR SEQ ID NO:39:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

Arg Asp Ala Pro Ala Ala Pro Ala Gly Val Pro Val Leu Asp
1               5                  10

(2) INFORMATION FOR SEQ ID NO:40:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

Asp Ala Pro Ala Ala Pro Ala Gly Pro Ala Val Pro Val
1               5                  10

(2) INFORMATION FOR SEQ ID NO:41:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

Asp Ala Ala Ala Pro Ala Gly Ala Pro Val Val

```
1               5                   10
```

(2) INFORMATION FOR SEQ ID NO:42:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

```
Asp Ala Pro Ala Ala Pro Ala Val Pro Val
1               5                   10
```

(2) INFORMATION FOR SEQ ID NO:43:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

```
Asp Ala Ala Pro Ala Ala Pro Val Val
1               5
```

(2) INFORMATION FOR SEQ ID NO:44:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

```
Asp Ala Pro Ala Ala Pro Val Val
1               5
```

(2) INFORMATION FOR SEQ ID NO:45:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

```
Asp Ala Ala Pro Val Val Pro
1               5
```

(2) INFORMATION FOR SEQ ID NO:46:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
Asp Ala Ala Pro Val Val
1               5
```

(2) INFORMATION FOR SEQ ID NO:47:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

```
Ala Ala Pro Val Val
1           5
```

(2) INFORMATION FOR SEQ ID NO:48:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

```
Arg Asp Leu Gly Phe Phe Pro Val Pro Gly Asp
1               5                   10
```

(2) INFORMATION FOR SEQ ID NO:49:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

```
Val His Val Ser Glu Glu Gly Thr Glu Pro Ala
1               5                   10
```

(2) INFORMATION FOR SEQ ID NO:50:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

```
Lys Lys Pro Val Phe Phe Ala Glu Asp
1               5
```

(2) INFORMATION FOR SEQ ID NO:51:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

```
Lys Lys Leu Pro Phe Phe Ala Glu Asp
1               5
```

(2) INFORMATION FOR SEQ ID NO:52:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

```
Lys Lys Leu Val Pro Phe Ala Glu Asp
1               5
```

(2) INFORMATION FOR SEQ ID NO:53:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

```
Lys Lys Leu Val Phe Pro Ala Glu Asp
1               5
```

(2) INFORMATION FOR SEQ ID NO:54:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:54:

```
Lys Lys Leu Val Phe Phe Pro Glu Asp
1               5
```

(2) INFORMATION FOR SEQ ID NO:55:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

```
Val His His Gln Lys Leu Val Pro Phe Ala Glu Asp Val Gly Ser
1               5                   10                  15
```

(2) INFORMATION FOR SEQ ID NO:56:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

Val Pro His Gln Lys Leu Val Phe Phe Ala Glu Asp Val Gly Ser
1               5                   10                  15

(2) INFORMATION FOR SEQ ID NO:57:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

Val His Pro Gln Lys Leu Val Phe Phe Ala Glu Asp Val Gly Ser
1               5                   10                  15

(2) INFORMATION FOR SEQ ID NO:58:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

Val His His Pro Lys Leu Val Phe Phe Ala Glu Asp Val Gly Ser
1               5                   10                  15

(2) INFORMATION FOR SEQ ID NO:59:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:59:

Val His His Gln Pro Leu Val Phe Phe Ala Glu Asp Val Gly Ser
1               5                   10                  15

(2) INFORMATION FOR SEQ ID NO:60:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:60:

Val His His Gln Lys Leu Val Phe Phe Ala Pro Asp Val Gly Ser
1               5                   10                  15

(2) INFORMATION FOR SEQ ID NO:61:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

Val His His Gln Lys Leu Val Phe Phe Ala Glu Pro Val Gly Ser
1               5                   10                  15

(2) INFORMATION FOR SEQ ID NO:62:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:62:

Val His His Gln Lys Val Leu Phe Phe Ala Glu Asp Pro Gly Ser
1               5                   10                  15

(2) INFORMATION FOR SEQ ID NO:63:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

Val His His Gln Lys Leu Val Phe Phe Ala Glu Asp Val Pro Ser
1               5                   10                  15

(2) INFORMATION FOR SEQ ID NO:64:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

Lys Lys Leu Val Phe Phe Ala Glu Asp
1               5

(2) INFORMATION FOR SEQ ID NO:65:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:65:

Val His His Gln Lys Leu Val Phe Phe Ala Glu Asp Val Gly Ser
1               5                   10                  15

(2) INFORMATION FOR SEQ ID NO:66:

(i) SEQUENCE CHARACTERISTICS:
        (A) LENGTH: 11 amino acids
        (B) TYPE: amino acid
        (C) STRANDEDNESS: single
        (D) TOPOLOGY: linear -continued (ii) MOLECULE TYPE: peptide (xi) SEQUENCE DESCRIPTION: SEQ ID NO:66:

Gly Tyr Leu Thr Val Ala Ala Val Phe Arg Gly
1               5                   10

(2) INFORMATION FOR SEQ ID NO:67:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

Pro Ala Asp Val Pro Leu Ala Pro Arg Ala Val Asp
1               5                   10

(2) INFORMATION FOR SEQ ID NO:68:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:68:

Tyr Glu Val His His Gln Lys Leu Val Phe Phe
1               5                   10

(2) INFORMATION FOR SEQ ID NO:69:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) FEATURE:
            'Xaa' in position one is a cationic amino acid
            'Xaa' in position two is a cationic amino acid
            'Xaa' in position three is a neutral amino acid
            'Xaa' in position four is a cationic amino acid (xi) SEQUENCE DESCRIPTION: SEQ ID NO:69:

Xaa Xaa Xaa Xaa